United States Patent
Altman et al.

(10) Patent No.: US 9,284,584 B2
(45) Date of Patent: Mar. 15, 2016

(54) METHOD FOR PRODUCING AN L-AMINO ACID USING A BACTERIUM OF THE FAMILY ENTEROBACTERIACEAE HAVING ENHANCED EXPRESSION OF THE FLAGELLA FORMATION AND MOTILITY CASCADE GENES

(71) Applicant: AJINOMOTO CO., INC., Tokyo (JP)

(72) Inventors: Irina Borisovna Altman, Moscow (RU); Tatyana Abramovna Yampolskaya, Moscow (RU); Leonid Romanovich Ptitsyn, Moscow (RU)

(73) Assignee: AJINOMOTO CO., INC., Tokyo (JP)

( * ) Notice: Subject to any disclaimer, the term of this patent is extended or adjusted under 35 U.S.C. 154(b) by 136 days.

(21) Appl. No.: 14/177,538

(22) Filed: Feb. 11, 2014

(65) Prior Publication Data

US 2014/0162325 A1  Jun. 12, 2014

Related U.S. Application Data

(63) Continuation of application No. PCT/JP2012/070947, filed on Aug. 14, 2012.

(30) Foreign Application Priority Data

Aug. 18, 2011  (RU) ................................ 2011134436

(51) Int. Cl.
*C07K 14/24* (2006.01)
*C12P 13/08* (2006.01)
*C07K 14/245* (2006.01)
*C12P 13/04* (2006.01)
*C12P 13/22* (2006.01)

(52) U.S. Cl.
CPC ................. *C12P 13/08* (2013.01); *C07K 14/24* (2013.01); *C07K 14/245* (2013.01); *C12P 13/04* (2013.01); *C12P 13/222* (2013.01)

(58) Field of Classification Search
CPC ........................................................ C07K 14/24
USPC ................................................. 435/106, 107
See application file for complete search history.

(56) References Cited

U.S. PATENT DOCUMENTS

| 5,830,716 | A | 11/1998 | Kojima et al. |
| 7,186,531 | B2 | 3/2007 | Akhverdian et al. |
| 7,915,018 | B2 | 3/2011 | Rybak et al. |
| 2007/0004014 | A1 | 1/2007 | Tsuji et al. |
| 2009/0162908 | A1 | 6/2009 | Yampolskaya et al. |
| 2009/0197309 | A1 | 8/2009 | Sycheva et al. |
| 2009/0203090 | A1 | 8/2009 | Ptitsyn et al. |
| 2014/0162325 | A1* | 6/2014 | Altman .................. C07K 14/24 435/107 |

FOREIGN PATENT DOCUMENTS

| WO | WO02/097089 | 12/2002 |
| WO | WO2006/078039 | 7/2006 |
| WO | WO2007/083788 | 7/2007 |
| WO | WO2007/119880 | 10/2007 |
| WO | WO2007/119890 | 10/2007 |
| WO | WO2013/024904 | 2/2013 |

OTHER PUBLICATIONS

Blumer, C., et al., "Regulation of type 1 fimbriae synthesis and biofilm formation by the transcriptional regulator LrhA of *Escherichia coli*," Microbiol. 2005;151:3287-3298.

Dong, X., et al., "Metabolic engineering of *Escherichia coli* and Corynebacterium glutamicum for the production of L-threonine," Biotechnol. Advances 2011;29:11-23.

Lehnen, D., et al., "LrhA as a new transcriptional key regulator of flagella, motility and chemotaxis genes in *Escherichia coli*," Molecular Microbiol. 2002;45(2):521-532.

Pesavento, C., et al., "Inverse regulatory coordination of motility and curli-mediated adhesion in *Escherichia coli*," Genes Dev. 2008;22:2434-2446.

Smith, T. G., et al., "Deciphering Bacterial Flagellar Gene Regulatory Networks in the Genomic Era," Adv. Appl. Microbiol. 2009;67:257-295.

Soutourina, O. A., et al., "Regulation cascade of flagellar expression in Gram-negative bacteria," FEMS Microbiol. Rev. 2003;27:505-523.

Sprenger, G. A., "From scratch to value: engineering *Escherichia coli* wild type cells to the production of L-phenylalanine and other fine chemicals derived from chorismate," Appl. Microbiol. Biotechnol. 2007;75:739-749.

Terashima, H., et al., "Flagellar Motility in Bacteria: Structure and Function to Flagellar Motor," Int. Rev. Cell Mol. Biol. 2008;270:39-85.

Yakandawala, N., et al., "Metabolic engineering of *Escherichia coli* to enhance phenylalanine production," Appl. Microbiol. Biotechnol. 2008;78:283-291.

International Search Report for PCT Patent App. No. PCT/JP2012/070947 (Jan. 11, 2013).

Written Opinion for PCT Patent App. No. PCT/JP2012/070947 (Jan. 11, 2013).

\* cited by examiner

*Primary Examiner* — Tekchand Saidha

(74) *Attorney, Agent, or Firm* — Shelly Guest Cermak; Cermak Nakajima & McGowan LLP

(57) ABSTRACT

The present invention provides a method for producing L-amino acid using a bacterium belonging to the family Enterobacteriaceae, particularly a motile bacterium belonging to the genus *Escherichia*, *Enterobacter* or *Pantoea*, wherein the bacterium has been modified so that expression of at least one gene of the flagella formation and motility cascade is enhanced.

10 Claims, 2 Drawing Sheets

SEQUENCE LISTING

```
<160> NUMBER OF SEQ ID NOS: 26

<210> SEQ ID NO 1
<211> LENGTH: 351
<212> TYPE: DNA
<213> ORGANISM: Escherichia coli

<400> SEQUENCE: 1
atgcataccT ccgagttgct gaaacacatt tatgacatca acttgtcata tttactactt      60
gcacagcgtt tgattgttca ggacaaagcg tccgctatgt ttcgtctcgg cataaatgaa     120
gaaatggcga caacgttagc ggcactgact cttccgcaaa tggttaagct ggcagaaacc     180
aatcaactgg tttgtcactt ccgttttgac agccaccaga cgattactca gttgacgcaa     240
gattcccgcg ttgacgatct ccagcaaatt cataccggca tcatgctctc aacacgcttg     300
ctgaatgatg ttaatcagcc tgaagaagcg ctgcgcaaga aagggcctg a               351

<210> SEQ ID NO 2
<211> LENGTH: 116
<212> TYPE: PRT
<213> ORGANISM: Escherichia coli

<400> SEQUENCE: 2

Met His Thr Ser Glu Leu Leu Lys His Ile Tyr Asp Ile Asn Leu Ser
1               5                   10                  15

Tyr Leu Leu Ala Gln Arg Leu Ile Val Gln Asp Lys Ala Ser Ala
            20                  25                  30

Met Phe Arg Leu Gly Ile Asn Glu Glu Met Ala Thr Thr Leu Ala Ala
        35                  40                  45

Leu Thr Leu Pro Gln Met Val Lys Leu Ala Glu Thr Asn Gln Leu Val
    50                  55                  60

Cys His Phe Arg Phe Asp Ser His Gln Thr Ile Thr Gln Leu Thr Gln
65                  70                  75                  80

Asp Ser Arg Val Asp Asp Leu Gln Gln Ile His Thr Gly Ile Met Leu
                85                  90                  95

Ser Thr Arg Leu Leu Asn Asp Val Asn Gln Pro Glu Glu Ala Leu Arg
            100                 105                 110

Lys Lys Arg Ala
        115

<210> SEQ ID NO 3
```

<211> LENGTH: 579
<212> TYPE: DNA
<213> ORGANISM: Escherichia coli

<400> SEQUENCE: 3

```
atgagtgaaa aaagcattgt tcaggaagcg cgggatattc agctggcaat ggaattgatc      60
accctgggcg ctcgtttgca gatgctggaa agcgaaacac agttaagtcg cggacgcctg     120
ataaaacttt ataagaact gcgcggaagc ccaccgccga aaggcatgct gccattctca     180
accgactggt ttatgacctg gaacaaaac gttcatgctt cgatgttctg taatgcatgg     240
cagtttttac tgaaaaccgg tttgtgtaat ggcgtcgatg cggtgatcaa agcctaccgt     300
ttatacctg aacagtgccc acaagcagaa gaaggaccac tgctggcatt aacccgtgcc     360
tggacattgg tgcggtttgt tgaaagtgga ttactgcaac tttccagctg caactgctgc     420
ggcggcaatt ttattaccca cgctcaccag cctgttggca gctttgcctg cagcttatgt     480
caaccgccat cccgggcagt aaaaagacgt aaactttccc agaatcctgc cgatattatc     540
ccacaactgc tggatgaaca gagagtacag gctgtttaa                            579
```

<210> SEQ ID NO 4
<211> LENGTH: 192
<212> TYPE: PRT
<213> ORGANISM: Escherichia coli

<400> SEQUENCE: 4

```
Met Ser Glu Lys Ser Ile Val Gln Glu Ala Arg Asp Ile Gln Leu Ala
1               5                   10                  15
Met Glu Leu Ile Thr Leu Gly Ala Arg Leu Gln Met Leu Glu Ser Glu
            20                  25                  30
Thr Gln Leu Ser Arg Gly Arg Leu Ile Lys Leu Tyr Lys Glu Leu Arg
        35                  40                  45
Gly Ser Pro Pro Lys Gly Met Leu Pro Phe Ser Thr Asp Trp Phe
    50                  55                  60
Met Thr Trp Glu Gln Asn Val His Ala Ser Met Phe Cys Asn Ala Trp
65                  70                  75                  80
Gln Phe Leu Leu Lys Thr Gly Leu Cys Asn Gly Val Asp Ala Val Ile
                85                  90                  95
Lys Ala Tyr Arg Leu Tyr Leu Glu Gln Cys Pro Gln Ala Glu Glu Gly
            100                 105                 110
Pro Leu Leu Ala Leu Thr Arg Ala Trp Thr Leu Val Arg Phe Val Glu
        115                 120                 125
Ser Gly Leu Leu Gln Leu Ser Ser Cys Asn Cys Gly Gly Asn Phe
    130                 135                 140
Ile Thr His Ala His Gln Pro Val Gly Ser Phe Ala Cys Ser Leu Cys
145                 150                 155                 160
Gln Pro Pro Ser Arg Ala Val Lys Arg Arg Lys Leu Ser Gln Asn Pro
                165                 170                 175
Ala Asp Ile Ile Pro Gln Leu Leu Asp Glu Gln Arg Val Gln Ala Val
            180                 185                 190
```

<210> SEQ ID NO 5
<211> LENGTH: 768
<212> TYPE: DNA
<213> ORGANISM: Escherichia coli

<400> SEQUENCE: 5

```
atgataaggc aggttatcca gcgaataagc aaccctgaag caagcatcga gagcttgcag      60
```

```
gaacggcgtt tttggttgca gtgtgagcgt gcttacacct ggcagccgat ctatcaaaca    120
tgcgggcggt taatggccgt ggagctatta acgtggtca cgcatccctt gaacccttcg    180
caacgcctgc cgccggatcg ctattttact gaaatcaccg tcagccatcg gatggaggtt    240
gtgaaagagc agattgattt gctggcgcaa aaagccgact tctttataga gcacggcctg    300
ctggcatcgg tcaatattga tggccctacg ctcatcgccc tgcgtcagca accaaaaatc    360
ctgcgccaga ttgagcgtct tccctggctg cgtttcgaac tggtggagca tatccgtctg    420
ccgaaagatt caacctttgc ctcgatgtgt gaatttggcc cgctgtggct ggatgatttt    480
ggtaccggga tggcaaattt ctctgcgcta agtgaagtgc gttatgacta catcaaaatc    540
gcgcgagaac tgtttgtgat gctgcgtcag tcgccggaag gacgcacact cttttctcag    600
cttttcatcc taatgaatcg ctattgtcgc ggggtgattg tcgagggcgt agaaacgccg    660
gaagagtggc gtgatgttca gaactcgccc gcattcgccg cacaaggctg gtttctttca    720
cgcccggcac cgatagaaac gctgaatacg gcggttctgg cgctataa                 768
```

<210> SEQ ID NO 6
<211> LENGTH: 255
<212> TYPE: PRT
<213> ORGANISM: Escherichia coli

<400> SEQUENCE: 6

```
Met Ile Arg Gln Val Ile Gln Arg Ile Ser Asn Pro Glu Ala Ser Ile
1               5                  10                  15

Glu Ser Leu Gln Glu Arg Arg Phe Trp Leu Gln Cys Glu Arg Ala Tyr
            20                  25                  30

Thr Trp Gln Pro Ile Tyr Gln Thr Cys Gly Arg Leu Met Ala Val Glu
        35                  40                  45

Leu Leu Thr Val Val Thr His Pro Leu Asn Pro Ser Gln Arg Leu Pro
    50                  55                  60

Pro Asp Arg Tyr Phe Thr Glu Ile Thr Val Ser His Arg Met Glu Val
65                  70                  75                  80

Val Lys Glu Gln Ile Asp Leu Leu Ala Gln Lys Ala Asp Phe Phe Ile
                85                  90                  95

Glu His Gly Leu Leu Ala Ser Val Asn Ile Asp Gly Pro Thr Leu Ile
            100                 105                 110

Ala Leu Arg Gln Gln Pro Lys Ile Leu Arg Gln Ile Glu Arg Leu Pro
        115                 120                 125

Trp Leu Arg Phe Glu Leu Val Glu His Ile Arg Leu Pro Lys Asp Ser
    130                 135                 140

Thr Phe Ala Ser Met Cys Glu Phe Gly Pro Leu Trp Leu Asp Asp Phe
145                 150                 155                 160

Gly Thr Gly Met Ala Asn Phe Ser Ala Leu Ser Glu Val Arg Tyr Asp
                165                 170                 175

Tyr Ile Lys Ile Ala Arg Glu Leu Phe Val Met Leu Arg Gln Ser Pro
            180                 185                 190

Glu Gly Arg Thr Leu Phe Ser Gln Leu Leu His Leu Met Asn Arg Tyr
        195                 200                 205

Cys Arg Gly Val Ile Val Glu Gly Val Glu Thr Pro Glu Glu Trp Arg
    210                 215                 220

Asp Val Gln Asn Ser Pro Ala Phe Ala Ala Gln Gly Trp Phe Leu Ser
225                 230                 235                 240

Arg Pro Ala Pro Ile Glu Thr Leu Asn Thr Ala Val Leu Ala Leu
```

<210> SEQ ID NO 7
<211> LENGTH: 552
<212> TYPE: DNA
<213> ORGANISM: Escherichia coli

<400> SEQUENCE: 7

```
atgatggtgc agcacctgaa aagacggcca ttaagccgct atcttaaaga ctttaaacac      60
agccagaccc attgcgcgca ttgccgtaaa ttactcgatc gcattacctt agttcgcgac     120
ggcaaaatag tgaataaaat cgagatttcc cgcctggaca cgctgcttga tgaaaatggc     180
tggcaaacgg aacaaaaatc atgggcggca ttgtgccgat tttgcggtga tttacattgc     240
aaaacgcaga gtgatttttt cgatattatc ggctttaagc aatttctttt tgagcaaact     300
gaaatgagcc caggtacggt gcgtgaatat gtcgttcgtt tgcgccgttt ggggaatcat     360
ctacacgagc aaaatatttc cctcgatcag ctgcaggacg gtttccttga tgaaatcctc     420
gccccgtggc tgcccaccac cagcaccaac aattaccgca tcgcgttacg gaagtatcaa     480
cactatcagc gccaaacctg taccagactt gtgcagaaat cctccagcct gccttcttct     540
gatatatatt aa                                                         552
```

<210> SEQ ID NO 8
<211> LENGTH: 183
<212> TYPE: PRT
<213> ORGANISM: Escherichia coli

<400> SEQUENCE: 8

```
Met Met Val Gln His Leu Lys Arg Arg Pro Leu Ser Arg Tyr Leu Lys
1               5                   10                  15
Asp Phe Lys His Ser Gln Thr His Cys Ala His Cys Arg Lys Leu Leu
            20                  25                  30
Asp Arg Ile Thr Leu Val Arg Asp Gly Lys Ile Val Asn Lys Ile Glu
        35                  40                  45
Ile Ser Arg Leu Asp Thr Leu Leu Asp Glu Asn Gly Trp Gln Thr Glu
    50                  55                  60
Gln Lys Ser Trp Ala Ala Leu Cys Arg Phe Cys Gly Asp Leu His Cys
65                  70                  75                  80
Lys Thr Gln Ser Asp Phe Phe Asp Ile Ile Gly Phe Lys Gln Phe Leu
                85                  90                  95
Phe Glu Gln Thr Glu Met Ser Pro Gly Thr Val Arg Glu Tyr Val Val
            100                 105                 110
Arg Leu Arg Arg Leu Gly Asn His Leu His Glu Gln Asn Ile Ser Leu
        115                 120                 125
Asp Gln Leu Gln Asp Gly Phe Leu Asp Glu Ile Leu Ala Pro Trp Leu
    130                 135                 140
Pro Thr Thr Ser Thr Asn Asn Tyr Arg Ile Ala Leu Arg Lys Tyr Gln
145                 150                 155                 160
His Tyr Gln Arg Gln Thr Cys Thr Arg Leu Val Gln Lys Ser Ser Ser
                165                 170                 175
Leu Pro Ser Ser Asp Ile Tyr
            180
```

<210> SEQ ID NO 9
<211> LENGTH: 42
<212> TYPE: DNA
<213> ORGANISM: Artificial Sequence -continued

```
<220> FEATURE:
<223> OTHER INFORMATION: Primer P1

<400> SEQUENCE: 9
cagagatttt gagacacaac gttcgtgtcg ctcaaggcgc ac                              42

<210> SEQ ID NO 10
<211> LENGTH: 69
<212> TYPE: DNA
<213> ORGANISM: Artificial Sequence
<220> FEATURE:
<223> OTHER INFORMATION: Primer P2

<400> SEQUENCE: 10
atgtcataaa tgtgtttcag caactcggag gtatgcatgg tctgtttcct gtgtgaaatt          60
ttatccgct                                                                  69

<210> SEQ ID NO 11
<211> LENGTH: 63
<212> TYPE: DNA
<213> ORGANISM: Artificial Sequence
<220> FEATURE:
<223> OTHER INFORMATION: Primer P3

<400> SEQUENCE: 11
atgtgcgtgt agtgacgagt acagttgcgt cgatttagga atcagaaaaa ctcatcgagc          60
atc                                                                        63

<210> SEQ ID NO 12
<211> LENGTH: 42
<212> TYPE: DNA
<213> ORGANISM: Artificial Sequence
<220> FEATURE:
<223> OTHER INFORMATION: Primer P4

<400> SEQUENCE: 12
tctcgccttg agcgacacga acgttgtgtc tcaaaatctc tg                             42

<210> SEQ ID NO 13
<211> LENGTH: 24
<212> TYPE: DNA
<213> ORGANISM: Artificial Sequence
<220> FEATURE:
<223> OTHER INFORMATION: Primer P5

<400> SEQUENCE: 13
ctgcatgaca aagtcatcgg gcat                                                 24

<210> SEQ ID NO 14
<211> LENGTH: 24
<212> TYPE: DNA
<213> ORGANISM: Artificial Sequence
<220> FEATURE:
<223> OTHER INFORMATION: Primer P6

<400> SEQUENCE: 14
tccgcgactt aactgtgttt cgct                                                 24

<210> SEQ ID NO 15
<211> LENGTH: 61
<212> TYPE: DNA
<213> ORGANISM: Artificial Sequence
<220> FEATURE:
<223> OTHER INFORMATION: Primer P7
```

<400> SEQUENCE: 15
cgggtgatgc tgccaactta cttttgagcc agaacgtatt cctgaaagat tccgttgtgg    60
a                                                                    61

<210> SEQ ID NO 16
<211> LENGTH: 71
<212> TYPE: DNA
<213> ORGANISM: Artificial Sequence
<220> FEATURE:
<223> OTHER INFORMATION: Primer P8

<400> SEQUENCE: 16
ataatcctag aataattccc gggcatttgc ccgggatgat gatagtccag ccaggcggaa    60
aatgaggcag c                                                         71

<210> SEQ ID NO 17
<211> LENGTH: 63
<212> TYPE: DNA
<213> ORGANISM: Artificial Sequence
<220> FEATURE:
<223> OTHER INFORMATION: Primer P9

<400> SEQUENCE: 17
agccaacgga taagcaatat tagctgactg atggtggcgg ttcagaaaaa ctcatcgagc    60
atc                                                                  63

<210> SEQ ID NO 18
<211> LENGTH: 61
<212> TYPE: DNA
<213> ORGANISM: Artificial Sequence
<220> FEATURE:
<223> OTHER INFORMATION: Primer P10

<400> SEQUENCE: 18
tccacaacgg aatctttcag gaatacgttc tggctcaaaa gtaagttggc agcatcaccc    60
g                                                                    61

<210> SEQ ID NO 19
<211> LENGTH: 20
<212> TYPE: DNA
<213> ORGANISM: Artificial Sequence
<220> FEATURE:
<223> OTHER INFORMATION: Primer P11

<400> SEQUENCE: 19
ctctctcaag gtcaaccgat                                                20

<210> SEQ ID NO 20
<211> LENGTH: 23
<212> TYPE: DNA
<213> ORGANISM: Artificial Sequence
<220> FEATURE:
<223> OTHER INFORMATION: Primer P12

<400> SEQUENCE: 20
gccagtctac aagggaccat caa                                            23

<210> SEQ ID NO 21
<211> LENGTH: 72
<212> TYPE: DNA
<213> ORGANISM: Artificial Sequence
<220> FEATURE:
<223> OTHER INFORMATION: Primer P13

```
<400> SEQUENCE: 21
atcattaaga actcctggta gtcaaagtta aagtgcggca tggtctgttt cctgtgtgaa      60
attttatccg ct                                                          72

<210> SEQ ID NO 22
<211> LENGTH: 42
<212> TYPE: DNA
<213> ORGANISM: Artificial Sequence
<220> FEATURE:
<223> OTHER INFORMATION: Primer P14

<400> SEQUENCE: 22
cgggtgatgc tgccaactta cttcgtgtcg ctcaaggcgc ac                          42

<210> SEQ ID NO 23
<211> LENGTH: 63
<212> TYPE: DNA
<213> ORGANISM: Artificial Sequence
<220> FEATURE:
<223> OTHER INFORMATION: Primer P15

<400> SEQUENCE: 23
aggctattaa acggttacgc actaaactgg gtaagttata atcagaaaaa ctcatcgagc      60
atc                                                                    63

<210> SEQ ID NO 24
<211> LENGTH: 42
<212> TYPE: DNA
<213> ORGANISM: Artificial Sequence
<220> FEATURE:
<223> OTHER INFORMATION: Primer P16

<400> SEQUENCE: 24
gtgcgccttg agcgacacga agtaagttgg cagcatcacc cg                         42

<210> SEQ ID NO 25
<211> LENGTH: 23
<212> TYPE: DNA
<213> ORGANISM: Artificial Sequence
<220> FEATURE:
<223> OTHER INFORMATION: Primer P17

<400> SEQUENCE: 25
ctggttactg atgatcatca gcg                                              23

<210> SEQ ID NO 26
<211> LENGTH: 24
<212> TYPE: DNA
<213> ORGANISM: Artificial Sequence
<220> FEATURE:
<223> OTHER INFORMATION: Primer P18

<400> SEQUENCE: 26
gcgaactaag gtaatgcgat cgag                                             24
```

METHOD FOR PRODUCING AN L-AMINO ACID USING A BACTERIUM OF THE FAMILY ENTEROBACTERIACEAE HAVING ENHANCED EXPRESSION OF THE FLAGELLA FORMATION AND MOTILITY CASCADE GENES

This application is a Continuation of, and claims priority under 35 U.S.C. §120 to, International Application No. PCT/JP2012/070947, filed Aug. 14, 2012, and claims priority therethrough under 35 U.S.C. §119 to Russian Patent Application No. 2011134436, filed Aug. 18, 2011, the entireties of which are incorporated by reference herein. Also, the Sequence Listing filed electronically herewith is hereby incorporated by reference (File name: 2014-02-11T_US-485_Seq_List; File size: 14 KB; Date recorded: Feb. 11, 2014).

BACKGROUND OF THE INVENTION

1. Field of Invention

The present invention relates to the microbiological industry, more specifically to a bacterium of the family Enterobacteriaceae in which expression of gene(s) associated with the flagella formation and motility cascade is/are deregulated, and a method for producing an L-amino acid by fermentation of the above bacteria in which expression of the flagella formation and motility cascade gene(s) is enhanced.

2. Brief Description of the Related Art

Conventionally, L-amino acids are industrially produced by fermentation methods utilizing strains of microorganisms obtained from natural sources, or mutants thereof. Typically, the microorganisms are modified to enhance production yields of L-amino acids.

Many techniques to enhance L-amino acid production yields have been reported, including transformation of microorganisms with recombinant DNA (see, for example, U.S. Pat. No. 4,278,765) and alteration of regulatory regions such as promoter, leader sequence and/or attenuator or others known to the person skilled in the art (see, for example, US20060216796 and WO9615246A1). Other techniques for enhancing production yields include increasing the activities of enzymes involved in amino acid biosynthesis and/or desensitizing the target enzymes to the feedback inhibition by the resulting L-amino acid (see, for example, WO9516042A1, EP0685555A1 or U.S. Pat. Nos. 4,346,170, 5,661,012 and 6,040,160).

Strains useful in production of L-threonine by fermentation are known, including strains with increased activities of enzymes involved in L-threonine biosynthesis (EP0219027A2 or U.S. Pat. Nos. 5,175,107; 5,661,012; 5,705,371; 5,939,307), strains resistant to chemicals such as L-threonine and its analogs (WO0114525A1, EP301572A2, U.S. Pat. No. 5,376,538), strains with target enzymes desensitized to the feedback inhibition by the produced L-amino acid or its by-products (U.S. Pat. Nos. 5,175,107 and 5,661,012), and strains with inactivated threonine degradation enzymes (U.S. Pat. Nos. 5,939,307 and 6,297,031).

It is described in the literature that motile bacteria such as *Salmonella typhimurium*, *Escherichia coli*, *Bacillus subtilis*, *Yersinia enterocolitica*, and the like can exhibit different lifestyles and can be in a motile single-cellular (or planktonic state) or can be sedentary cells that use adhesive fimbriae to cluster together and form biofilms on a surface (O'Toole G. A. et al., *Annu. Rev. Microbiol.*, 2000: 54, 49-79). *Escherichia coli* (*E. coli*) cells, for example, are highly motile during the post-exponential growth phase (Amsler C. D. et al., *J. Bacteriol.*, 1993: 175, 6238-6244), and become aggregated or adhere to a surface by the induction of adhesive curli fimbriae when entering into the stationary phase (Olsén A. et al., *Nature*, 1989: 338, 652-655).

It is known that in *E. coli* both flagella formation and motility, and curli-mediated adhesion cascades are under the control of regulatory feedforward cascades, each with a master regulator at the top, which acts as a massive environmental signal integrator (Pesavento C. et al., *Gen. Dev.*, 2011: 22, 2434-2446). The curli fimbriae control cascade is a module within the general stress response, for which the $\sigma^S$ factor (sigmaS, RpoS) acts as the master regulator (Hengge-Aronis R. 2000. The general stress response in *E. coli*. In Bacterial stress responses (eds. G. Storz and R. Hengge-Aronis), pp. 161-178. ASM Press, Washington, D.C.). The CsgD protein was shown to be an essential activator for the curli structural gene operon (csgBAC) (Gerstel U. et al., *Mol. Microbiol.*, 2003: 49, 639-654).

For flagellar expression and motility cascade, the master regulator is the FlhDC complex expressed from flhDC operon defined as the flagella class 1 operon. The flagella master regulator FlhDC functions as a hetero-oligomeric complex of the FlhD and FlhC proteins (the $FlhD_4C_2$ complex), the crystallographic structure of which, originated from *E. coli*, was resolved (Wang S. et al., *J. Mol. Biol.*, 2006, 355:798-808). The FlhDC complex regulates transcription from several flagellar and non-flagellar operons in bacteria, and, in particular, it activates the expression of class 2 operons, which are responsible for the inner part of the flagella and various factors (FliA, FlgM) (Pesavento C. et al., *Gen. Dev.*, 2011: 22, 2434-2446). After the FlgM factor is secreted, FliA is released to activate class 3 operons which encode the outer subunits of additional flagella proteins required for flagellar function and chemotaxis, as well as a number of proteins of still unknown function (Aldrigde P. D. et al., *Gen. Dev.*, 2006: 20, 2315-2326).

Another key regulator of cell motility and curli fimbriae expression is bis-(3'-5')-cyclic-diguanosine monophosphate (c-di-GMP) degrading phosphodiesterase (PDE), for example, YhjH and YciR (the latter in addition to c-di-GMP PDE activity also functions in opposite direction as diguanilate cyclase). Overproduction of c-di-GMP PDE was demonstrated to interfere with motility of enteric bacteria through strong inactivation of expression of curli fimbriae and the biofilm matrix component cellulose (Römling U. et al., *Mol. Microbiol.*, 2005: 57, 629-639; Jenal U. and Malone J., *Annu. Rev. Genet.*, 2006: 40, 385-407). In a particular case, YhjH was shown to play a positive role in motility (Ko M. and Park C., *J. Mol. Biol.*, 2000: 303, 371-382).

The FliZ protein, which is expressed from a gene immediately downstream from fliA, was demonstrated to be a highly potent inhibitor of curli fimbriae formation in *E. coli* by interfering with the activity of $\sigma^S$ factor which controls genes involved in curli expression (Pesavento C. et al., *Gen. Dev.*, 2011: 22, 2434-2446). More specifically, FliZ transiently gives motility (and therefore a foraging strategy) priority over the general stress response as long as flagellar gene expression keeps going.

A bacterium of the family Enterobacteriaceae, which has been modified to attenuate expression of the csgBAC or/and csgDEFG operons (RU2338782) or so as to not produce type I fimbrial adhesin protein (EP1838726A1), has been employed for producing an L-amino acid, specifically, L-threonine.

Furthermore, it is known from WO2002097089A1 that flagella-containing microorganisms, in which one or more genes relating to the constitution of flagella or movement of flagella is/are inactivated or deleted, can be used as hosts for producing useful substances, for example, amino acids (WO2002097089A1).

Until now, there have been no reports highlighting positive effect of enhanced expression of bacterial genes (flhDC, yhjH and flit) involved in the flagella formation and motility cascade on the productivity of L-amino acids, and more specifically L-threonine and L-phenylalanine.

SUMMARY OF THE INVENTION

Aspects of the present invention include to provide a bacterium belonging to the family Enterobacteriaceae, specifically to the genera *Escherichia, Enterobacter* and *Pantoea*, in which expression of the flagella formation and motility cascade gene(s) is/are enhanced, and a method for producing L-amino acids, specifically, L-threonine and L-phenylalanine using said bacterium. This aim was achieved by the finding that enhanced expression of the flagella formation and motility cascade gene(s), for example, the flhDC operon genes of *E. coli*, which encode DNA-binding transcriptional dual regulators FlhD and FlhC which are a part of the flagella master regulator $FlhD_4C_2$ complex, results in increased L-amino acid production. The inventors also found that increased production of L-amino acid can be achieved by using the flhDC operon genes in combination with other genes of the flagella formation and motility cascade such as yhjH and fliZ having enhanced expression.

It is an aspect of the present invention to provide a method for producing an L-amino acid comprising culturing a Enterobacteriaceae bacterium in a medium, and collecting the L-amino acid from the medium, wherein the bacterium is able to produce L-amino acid and has been modified so that expression of at least one gene of the flagella formation and motility cascade is enhanced.

It is a further aspect of the present invention to provide the method as described above, wherein said at least one gene is selected from the group consisting of the flhDC operon gene(s), the yhjH gene, the fliZ gene, and combinations thereof.

It is a further aspect of the present invention to provide the method as described above, wherein said expression of the gene(s) of the flhDC operon is enhanced by modifying an expression control region for the gene(s).

It is a further aspect of the present invention to provide the method as described above, wherein said expression of the gene(s) of the flhDC operon is enhanced by increasing the copy number of the gene(s).

It is a further aspect of the present invention to provide the method as described above, wherein said bacterium belongs to the genus *Escherichia*.

It is a further aspect of the present invention to provide the method as described above, wherein said bacterium is *Escherichia coli*.

It is a further aspect of the present invention to provide the method as described above, wherein said bacterium belongs to the genus *Enterobacter*.

It is a further aspect of the present invention to provide the method as described above, wherein said bacterium belongs to the genus *Pantoea*.

It is a further aspect of the present invention to provide the method as described above, wherein the flhD gene encodes a protein selected from the group consisting of:

(A) a protein comprising the amino acid sequence shown in SEQ ID NO: 2;

(B) a protein comprising the amino acid sequence shown in SEQ ID NO: 2, but wherein one or several amino acid residues are substituted, deleted, inserted, added or inverted, and said protein has DNA-binding transcriptional dual regulator activity according to the amino acid sequence of SEQ ID NO: 2; and (C) a combination thereof.

It is a further aspect of the present invention to provide the method as described above, wherein the flhC gene encodes a protein selected from the group consisting of:

(A) a protein comprising the amino acid sequence shown in SEQ ID NO: 4;

(B) a protein comprising the amino acid sequence shown in SEQ ID NO: 4, but wherein one or several amino acid residues are substituted, deleted, inserted, added or inverted, and said protein has DNA-binding transcriptional dual regulator activity according to the amino acid sequence of SEQ ID NO: 4; and (C) a combination thereof.

It is a further aspect of the present invention to provide the method as described above, wherein the yhjH gene encodes a protein selected from the group consisting of:

(A) a protein comprising the amino acid sequence shown in SEQ ID NO: 6;

(B) a protein comprising the amino acid sequence shown in SEQ ID NO: 6, but wherein one or several amino acid residues are substituted, deleted, inserted, added or inverted, and said protein has cyclic-di-GMP phosphodiesterase activity according to the amino acid sequence of SEQ ID NO: 6; and (C) a combination thereof.

It is a further aspect of the present invention to provide the method as described above, wherein the fliZ gene encodes a protein selected from the group consisting of:

(A) a protein comprising the amino acid sequence shown in SEQ ID NO: 8;

(B) a protein comprising the amino acid sequence shown in SEQ ID NO: 8, but wherein one or several amino acid residues are substituted, deleted, inserted, added or inverted, and said protein has regulator activity according to the amino acid sequence of SEQ ID NO: 8; and (C) a combination thereof.

It is a further aspect of the present invention to provide the method as described above, wherein the L-amino acid is aromatic L-amino acid.

It is a further aspect of the present invention to provide the method as described above, wherein the aromatic L-amino acid is selected from the group consisting of L-phenylalanine, L-tyrosine, L-tryptophan, and combinations thereof.

It is a further aspect of the present invention to provide the method as described above, wherein the L-amino acid is non-aromatic L-amino acid.

It is a further aspect of the present invention to provide the method as described above, wherein the non-aromatic L-amino acid is selected from the group consisting of L-threonine, L-lysine, L-cysteine, L-methionine, L-leucine, L-isoleucine, L-valine, L-histidine, L-serine, L-alanine, L-asparagine, L-aspartic acid, L-glutamine, L-glutamic acid, L-proline, L-arginine, glycine, and combinations thereof.

It is a further aspect of the present invention to provide the method as described above, wherein the L-amino acid is L-phenylalanine.

It is a further aspect of the present invention to provide the method as described above, wherein the L-amino acid is L-threonine.

DETAILED DESCRIPTION OF THE PREFERRED EMBODIMENTS

Figure 1:
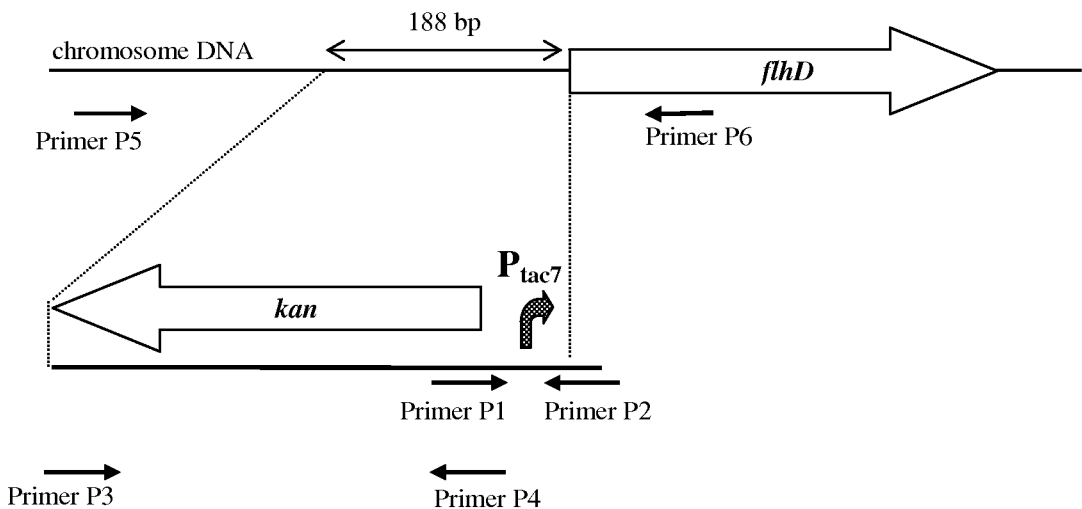
FIG. 1 is a scheme for the kan-$P_{tac7}$ DNA fragment construction.

The present invention is described in details below.

1. Bacterium according to the present invention

The phrase "an L-amino acid-producing bacterium" can mean a bacterium which has an ability to produce and cause accumulation of L-amino acid in a culture medium when the bacterium is cultured in the medium. The L-amino acid-producing ability can mean the ability of the bacterium to produce an L-amino acid in a medium or the bacterial cells and cause accumulation of the L-amino acid to such an extent that the L-amino acid can be collected from the medium or the bacterial cells, when the bacterium is cultured in the medium. The term "L-amino acid" can include L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, and L-valine.

The term "aromatic L-amino acid" can include L-phenylalanine, L-tyrosine, and L-tryptophan. The term "non-aromatic L-amino acid" can include L-threonine, L-lysine, L-cysteine, L-methionine, L-leucine, L-isoleucine, L-valine, L-histidine, L-serine, L-alanine, L-asparagine, L-aspartic acid, L-glutamine, L-glutamic acid, glycine, L-proline, and L-arginine. L-threonine, L-lysine, L-cysteine, L-leucine, L-histidine, L-glutamic acid, L-phenylalanine, L-tryptophan, L-proline, and L-arginine are particular examples.

The L-amino acid can include L-amino acids in free form and salts thereof, such as sulfates, hydrochlorides, carbonates, ammonium salts, sodium salts, and potassium salts.

The L-amino acid may be produced by the method of the present invention either alone or as a mixture of two or more kinds of L-amino acids The bacterium can inherently have the L-amino acid-producing ability or can be modified to have an L-amino acid-producing ability by using a mutation method or DNA recombination techniques, as described herein.

The bacteria belonging to the family Enterobacteriaceae can include bacteria from the genera *Enterobacter, Erwinia, Escherichia, Morganella, Pantoea, Salmonella, Yersinia*, and so forth, and having the aforementioned L-amino acid-producing ability. Specifically, those classified into the family Enterobacteriaceae according to the taxonomy used in the NCBI (National Center for Biotechnology Information) database (www.ncbi.nlm.nih.gov/Taxonomy/Browser/wwwtax.cgi?id=543) can be used. Examples of strains from the family Enterobacteriaceae which can be modified as described herein include a bacterium of the genus *Escherichia, Enterobacter* or *Pantoea*.

Strains of *Escherichia* bacterium which can be modified to obtain *Escherichia* bacteria in accordance with the presently disclosed subject matter are not particularly limited, and specifically, those described in the work of Neidhardt et al. can be used (Bachmann, B. J., Derivations and genotypes of some mutant derivatives of *E. coli* K-12, p. 2460-2488. In F. C. Neidhardt et al. (ed.), *E. coli* and *Salmonella*: cellular and molecular biology, $2^{nd}$ ed. ASM Press, Washington, D.C., 1996). The species *E. coli* is a particular example. Specific examples of *E. coli* include *E. coli* W3110 (ATCC 27325), *E. coli* MG1655 (ATCC 47076), and so forth, which are derived from the prototype wild-type strain, K-12 strain. These strains are available from, for example, the American Type Culture Collection (P.O. Box 1549, Manassas, Va. 20108, United States of America). That is, registration numbers are given to each of the strains, and the strains can be ordered by using these registration numbers (refer to www.atcc.org). The registration numbers of the strains are listed in the catalogue of the American Type Culture Collection.

Examples of the *Enterobacter* bacteria include *Enterobacter agglomerans, Enterobacter aerogenes*, and so forth. Examples of the *Pantoea* bacteria include *Pantoea ananatis*, and so forth. Some strains of *Enterobacter agglomerans* were recently reclassified into *Pantoea agglomerans, Pantoea ananatis* or *Pantoea stewartii* on the basis of nucleotide sequence analysis of 16S rRNA, etc. A bacterium belonging to any of the genus *Enterobacter* or *Pantoea* may be used so long as it is a bacterium classified into the family Enterobacteriaceae. When a *Pantoea ananatis* strain is bred by genetic engineering techniques, *Pantoea ananatis* AJ13355 strain (FERM BP-6614), AJ13356 strain (FERM BP-6615), AJ13601 strain (FERM BP-7207) and derivatives thereof can be used. These strains were identified as *Enterobacter agglomerans* when they were first isolated, and deposited as *Enterobacter agglomerans*. However, they were recently re-classified as *Pantoea ananatis* on the basis of nucleotide sequencing of 16S rRNA and so forth as described above.

The phrase "a motile bacterium" can mean a single-cellular or planktonic bacterium exhibiting, but is not limited, to self-propelled motion under appropriate circumstances using flagella or a flagellum being in or by entering into a definite growth phase when grown in a culture medium. Specifically, those described in "Bergey's Manual of Systematic Bacteriology" ($2^{nd}$ ed., Springer, New York) can be used. The phrase "a motile bacterium" also can mean a bacterium which possesses the ability and is able to move forward (swimming) through a culture medium with a velocity which is lower, equal to, or higher than wild-type or unmodified parent bacteria. The phrase "a motile bacterium" also can mean a bacterium which possesses the ability and is able to exist in the motile single-cellular or planktonic state for a period which is shorter, equal to, or longer than wild-type or unmodified parent bacteria.

The present invention can be achieved by enhancing or increasing the expression of genes associated with the flagella formation and motility cascade.

The phrase "genes associated with the flagella formation and motility cascade" can mean any gene or genes involved in the flagella formation and motility cascade, and which code for protein(s) directly or indirectly involved in functional flagella formation or assembling and stimulating or prolonging bacteria motility via various mechanisms. Examples of the genes associated with the flagella formation and motility cascade can be, but are not limited to, the genes of the flhDC operon encoding the flagella master regulator FlhD$_4$C$_2$ complex, which positively affects bacterial flagella formation. Other examples of the genes associated with the flagella formation and motility cascade include the yhjH gene encoding c-di-GMP PDE, which decreases the c-di-GMP pool in a bacterium, and the fliZ gene, which interferes with $\sigma^S$ activity.

The phrase "functional flagella" can mean correctly assembled flagella capable of rotation or another motion to allow a bacterium to be considered as a motile bacterium.

The phrase "at least one gene of the flagella formation and motility cascade" can mean one or more genes of the flagella formation and motility cascade, and can include, not limiting to, genes of the flhDC operon, yhjH, and fliZ genes in any combination".

The phrase "the flhDC operon, yhjH, and fliZ genes in any combination" can mean either one gene selected from the flhDC operon, yhjH and fliZ genes or two or more different genes selected from the flhDC operon, yhjH and fliZ genes, but is not limited to these combinations.

The phrase "modified so that expression of at least one gene of the flagella formation and motility cascade is enhanced" can mean that the number of the molecules encoded by the flhDC operon gene(s) and/or the yhjH gene and/or the fliZ gene per cell increases, or the activity per molecule (may be referred to as a specific activity) of the protein encoded by these genes improves, as compared with an unmodified strain, such as a wild-type or parent strain. The bacterium can be modified so that the activity of the protein per cell increases to 150% or more, 200% or more in another example, 300% or more in another example, of the activity of an unmodified strain. Examples of an unmodified strain serving as a reference for the above comparison, such as a wild-type strain of a microorganism belonging to the family Enterobacteriaceae, include, for example, the *E. coli* MG1655 strain (ATCC 47076), W3110 strain (ATCC 27325), *Pantoea ananatis* AJ13335 strain (FERM BP-6614), and so forth.

Methods which can be used to enhance expression of the gene(s) or operon genes include increasing the gene(s) or operon genes copy number and/or introducing the gene(s) or operon genes into a vector that is able to increase the copy number of the gene(s) or operon genes in a bacterium of the family Enterobacteriaceae. To enhance expression of the gene(s), the copy number of the gene can be increased in cells utilizing, for example, gene recombination techniques. The copy number of the gene can be increased by ligating a DNA fragment containing the gene to a vector which functions in the host bacterium, such as a multi copy vector, to prepare a recombinant DNA, and introducing it into the bacterium to transform the bacterium. Examples of autonomously replicable vectors in *E. coli* cells include pUC19, pUC18, pHSG299, pHSG399, pHSG398, pACYC184, (pHSG and pACYC series vectors are available from Takara Bio Inc.), RSF1010, pBR322, pMW219 (pMW219 is available form Nippon Gene Co., Ltd.), pSTV29 (available form Takara Bio Inc.), and so forth.

Enhancement of the gene(s) or operon gene's expression can also be achieved by introducing multiple copies of the gene(s) or operon genes into the chromosomal DNA of a bacterium by, for example, homologous recombination, Mu integration, or the like. Homologous recombination can be carried out using a sequence which is present in multiple copies in the chromosomal DNA. Sequences with multiple copies in the chromosomal DNA include but are not limited to repetitive DNA or inverted repeats present at the end of a transposable element. In addition, it is possible to incorporate the gene(s) or operon genes into a transposon and allow it to be transferred to introduce multiple copies of the gene(s) or operon genes into the chromosomal DNA. By using Mu integration, up to 3 copies of the gene can be introduced into the chromosomal DNA during a single act.

Enhancing of the gene(s) or operon genes expression may also be achieved by placing the DNAs under the control of a potent promoter. For example, the lac promoter, the trp promoter, the trc promoter, the tac promoter, the $P_R$ or the $P_L$ promoters of lambda phage are all known to be potent promoters. Potent promoters providing a high level of gene expression in a bacterium belonging to the family Enterobacteriaceae can be used. Alternatively, the effect of a promoter can be enhanced by, for example, introducing a mutation into the promoter region of the gene(s) or operon genes on the bacterial chromosome to obtain a stronger promoter function, thus resulting in the increased transcription level of the gene(s) or operon genes located downstream of the promoter. Furthermore, it is known that substitution of several nucleotides in the spacer between ribosome binding site (RBS) and the start codon, especially the sequences immediately upstream of the start codon, profoundly affect the mRNA translatability. For example, a 20-fold range in the expression levels was found, depending on the nature of the three nucleotides preceding the start codon (Gold L. et al., *Annu. Rev. Microbiol.*, 1981: 35, 365-403; Hui A. et al., *EMBO J.*, 1984: 3, 623-629). The use of a potent promoter can be combined with multiplication of gene copies.

Methods for preparation of plasmid DNA, digestion, ligation and transformation of DNA, selection of an oligonucleotide as a primer, and the like may be ordinary methods well-known to the person skilled in the art. These methods are described, for instance, in Sambrook J., Fritsch E. F. and Maniatis T., "Molecular Cloning: A Laboratory Manual, $2^{nd}$ ed.", Cold Spring Harbor Laboratory Press (1989). Methods for molecular cloning and heterologous gene expression are described in Bernard R. Glick, Jack J. Pasternak and Cheryl L. Patten, "Molecular Biotechnology: principles and applications of recombinant DNA", $4^{th}$ ed., Washington, D.C.: ASM Press (2009); Evans Jr., T. C. and Xu M.-Q., "Heterologous gene expression in *E. coli*", $1^{st}$ ed., Humana Press (2011).

The level of gene expression can be determined by measuring the amount of mRNA transcribed from the gene using various known methods including Northern blotting, quantitative RT-PCR, and the like. The amount of the protein coded by the gene can be measured by known methods including SDS-PAGE followed by immunoblotting assay (Western blotting analysis), and the like.

The gene of the flagella formation and motility cascade includes a gene selected from the flhDC operon, yhjH and fliZ genes.

The flhDC operon includes the two genes which are flhD and flhC.

The flhD gene encodes DNA-binding transcriptional dual regulator FlhD (KEGG, Kyoto Encyclopedia of Genes and Genomes, entry No. b1892). The flhD gene (GenBank accession No. NC_000913.2; nucleotide positions: 1,975,871 to 1,976,221, complement; Gene ID: 945442) is located between the flhC and insB genes on the chromosome of *E. coli* K-12. The nucleotide sequence of the flhD gene and the amino acid sequence of the FlhD protein encoded by the flhD gene are shown in SEQ ID NO: 1 and SEQ ID NO: 2, respectively.

The flhC gene encodes DNA-binding transcriptional dual regulator FlhC (KEGG, Kyoto Encyclopedia of Genes and Genomes, entry No. b1891). The flhC gene (GenBank accession No. NC_000913.2; nucleotide positions: 1,975,290 to 1,975,868, complement; Gene ID: 947280) is located between the motA and flhD genes on the chromosome of *E. coli* K-12. The nucleotide sequence of the flhC gene and the amino acid sequence of the FlhC protein encoded by the flhC gene are shown in SEQ ID NO: 3 and SEQ ID NO: 4, respectively.

The yhjH gene encodes cyclic-di-GMP phosphodiesterase YhjH (KEGG, Kyoto Encyclopedia of Genes and Genomes, entry No. b3525). The yhjH gene (GenBank accession No. NC_000913.2; nucleotide positions: 3,676,443 to 3,677,210, complement; Gene ID: 948042) is located between the yhjG and kdgK genes on the chromosome of *E. coli* K-12. The nucleotide sequence of the yhjH gene and the amino acid sequence of the YhjH protein encoded by the yhjH gene are shown in SEQ ID NO: 5 and SEQ ID NO: 6, respectively.

The fliZ gene encodes RpoS antagonist and putative regulator of FliA activity FliZ (KEGG, Kyoto Encyclopedia of Genes and Genomes, entry No. b1921). The fliZ gene (GenBank accession No. NC_000913.2; nucleotide positions: 1,998,497 to 1,999,048, complement; Gene ID: 946833) is located between the fllY and fliA genes on the chromosome of E. coli K-12. The nucleotide sequence of the fliZ gene and the amino acid sequence of the FliZ protein encoded by the fliZ gene are shown in SEQ ID NO: 7 and SEQ ID NO: 8, respectively.

Since there may be some differences in DNA sequences between the genera or strains of the family Enterobacteriaceae, each of the genes of flhDC operon and the genes yhjH and fliZ to be enhanced on the chromosome is not limited to the gene shown in SEQ ID NO: 1, 3, 5 or 7, but may include a gene homologous to SEQ ID NO: 1, 3, 5 or 7, which encode a variant of the FlhD, FlhC, YhjH or FliZ protein. The phrase "variant protein" can mean a protein which has changes in the sequence, whether they are deletions, insertions, additions substitutions, or inversions of one or several amino acid residues, but still maintains the activity similar to FlhD, FlhC, YhjH or FliZ protein, respectively. The number of changes in the variant protein depends on the position in the three dimensional structure of the protein or the type of amino acid residues. It can be 1 to 30, in another example 1 to 15 and in another example 1 to 5 in SEQ ID NO: 2, 4, 6 or 8.

The deletions, insertions, additions or substitutions of one or several amino acid residues can be conservative mutation(s) so that the activity of the protein encoded by the gene of the flhDC operon and the yhjH and fliZ genes is maintained. A representative conservative mutation can be a conservative substitution. The conservative substitution can be a substitution wherein substitution takes place mutually among Phe, Trp and Tyr, if the substitution site is an aromatic amino acid; among Leu, Ile and Val, if the substitution site is a hydrophobic amino acid; between Gln and Asn, if it is a polar amino acid; among Lys, Arg and His, if it is a basic amino acid; between Asp and Glu, if it is an acidic amino acid; and between Ser and Thr, if it is an amino acid having hydroxyl group. Specific examples of substitutions which are considered conservative substitutions include substitution of Ser or Thr for Ala; substitution of Gln, His or Lys for Arg; substitution of Glu, Gln, Lys, His or Asp for Asn; substitution of Asn, Glu or Gln for Asp; substitution of Ser or Ala for Cys; substitution of Asn, Glu, Lys, His, Asp or Arg for Gln; substitution of Gly, Asn, Gln, Lys or Asp for Glu; substitution of Pro for Gly; substitution of Asn, Lys, Gln, Arg or Tyr for His; substitution of Leu, Met, Val or Phe for Ile; substitution of Ile, Met, Val or Phe for Leu; substitution of Asn, Glu, Gln, His or Arg for Lys; substitution of Ile, Leu, Val or Phe for Met; substitution of Trp, Tyr, Met, Ile or Leu for Phe; substitution of Thr or Ala for Ser; substitution of Ser or Ala for Thr; substitution of Phe or Tyr for Trp; substitution of His, Phe or Trp for Tyr; and substitution of Met, Ile or Leu for Val. The mutation of such substitution, deletion, insertion, addition, inversion or the like of amino acid residues as described above can also include a naturally occurring mutation based on individual differences, differences in species of microorganisms having the genes of the flhDC operon and the yhjH and fliZ genes (mutant or variant) and so forth.

These changes in the variant can occur in regions of the protein which are not critical for the function of the protein. This is because some amino acids have high homology to one another so that the three dimensional structure or activity is not affected by such a change. Therefore, the protein variant encoded by each of the genes of flhDC operon, or the gene yhjH or fliZ may have a homology of not less than 80%, in another example not less than 90%, in another example not less than 95%, in another example not less than 97%, or in another example not less than 99% with respect to the entire amino acid sequences shown in SEQ ID NOs: 2, 4, 6 or 8 as long as the functionality of the FlhD or FlhC proteins, or the $FlhD_4C_2$ complex assembled from FlhD and FlhC proteins, and the YhjH or FlizH protein, as described above, is maintained. Homology between two amino acid sequences can be determined using the well-known methods, for example, the computer program BLAST (Basic Local Alignment Search Tool, www.ncbi.nlm.nih.gov/BLAST/), which calculates three parameters: score, identity and similarity.

Moreover, each of genes of the flhDC operon and the genes yhjH and fliZ can be a variant which hybridizes under stringent conditions with the nucleotide sequences complementary to sequences shown in SEQ ID NOs: 1, 3, 5 or 7, or a probe which can be prepared from the nucleotide sequence under stringent conditions provided that it encodes the functional FlhD or FlhC protein, or the $FlhD_4C_2$ complex assembled from FlhD and FlhC proteins, or the YhjH or FlizH protein prior to inactivation. "Stringent conditions" include those under which a specific hybrid, for example, a hybrid having homology of not less than 80%, in another example not less than 90%, in another example not less than 95%, in another example not less than 97% and in another example not less than 99% is formed and a non-specific hybrid, for example, a hybrid having homology lower than the above is not formed. For example, stringent conditions can be exemplified by washing one time or more, or in another example, two or three times at a salt concentration of 1×SSC, 0.1% SDS, or in another example, 0.1×SSC, 0.1% SDS at 60° C., or in another example, at 65° C. Duration of washing depends on the type of membrane used for blotting and, as a rule, should be what is recommended by the manufacturer. For example, the recommended duration of washing for the Amersham Hybond™-N+ positively charged nylon membrane (GE Healthcare) under stringent conditions is 15 minutes. The washing step can be performed 2 to 3 times. As the probe, a part of the sequence complementary to the sequences shown in SEQ ID NO: 1, 3, 5 or 7 may also be used. Such a probe can be produced by PCR using oligonucleotides as primers prepared on the basis of the sequences shown in SEQ ID NO: 1, 3, 5 or 7, and a DNA fragment containing the nucleotide sequence as a template. The length of the probe is recommended to be >50 bp; it can be suitably selected depending on the hybridization conditions, and is usually 100 bp to 1 kbp. For example, when a DNA fragment having a length of about 300 bp is used as the probe, the washing conditions after hybridization can be exemplified by 2×SSC, 0.1% SDS at 50° C., or at 60° C., or in another example, at 65° C.

As the genes coding for the FlhD, FlhC, YhjH and FliZ proteins of E. coli have already been elucidated (see above), they and their variant proteins can be obtained by PCR (polymerase chain reaction; refer to White T. J. et al., *Trends Genet.*, 1989: 5, 185-189) utilizing primers prepared based on the nucleotide sequence of the flhD, flhC, yhjH and fliZ gene, respectively. Genes coding for the FlhD, FlhC, YhjH and FliZ proteins or their variant proteins of other microorganisms can be obtained in a similar manner.

Methods for imparting the ability to produce an L-amino acid such as L-lysine, L-threonine, L-aspartic acid, L-asparagine, L-methionine, L-alanine, L-isoleucine and/or L-homoserine to bacteria belonging to the family Enterobacteriaceae, and methods for enhancing an ability to produce above-mentioned L-amino acids in bacteria belonging to the family Enterobacteriaceae are described below.

To impart the ability to produce an L-amino acid, methods conventionally employed in the breeding of coryneform bacteria or bacteria of the genus *Escherichia* can be used (see "Amino acid fermentation", Gakkai Shuppan Center (Ltd.), pp. 77-100, 1$^{st}$ ed., 1986). Such methods include by acquiring the properties of an auxotrophic mutant, an L-amino acid analogue-resistant strain, or a metabolic regulation mutant, or by constructing a recombinant strain so that it over-expresses an L-amino acid biosynthesis enzyme. Here, in the breeding of L-amino acid-producing bacteria, one or more of the above-described properties such as auxotrophy, analogue resistance, and metabolic regulation mutation can be imparted. The expression of L-amino acid biosynthesis enzyme(s) can be enhanced alone or in combinations of two or more. Furthermore, the methods of imparting properties such as an auxotrophy, analogue resistance, or metabolic regulation mutation can be combined with enhancement of the biosynthesis enzymes.

An auxotrophic mutant strain, L-amino acid analogue-resistant strain, or metabolic regulation mutant strain with the ability to produce an L-amino acid can be obtained by subjecting a parent or wild-type strain to conventional mutagenesis, such as exposure to X-rays or UV irradiation, or treatment with a mutagen such as N-methyl-N'-nitro-N-nitrosoguanidine (NTG) and ethyl methanesulfonate (EMS), then selecting strains which exhibit autotrophy, analogue resistance, or a metabolic regulation mutation and which also have the ability to produce an L-amino acid from the obtained mutant strains.

L-Threonine-Producing Bacteria

Examples of parent strains which can be used to derive the L-threonine-producing bacteria include but are not limited to strains belonging to the genus *Escherichia*, such as *E. coli* TDH-6/pVIC40 (VKPM B-3996) (U.S. Pat. No. 5,175,107, U.S. Pat. No. 5,705,371), *E. coli* 472T23/pYN7 (ATCC 98081) (U.S. Pat. No. 5,631,157), *E. coli* NRRL-21593 (U.S. Pat. No. 5,939,307), *E. coli* FERM BP-3756 (U.S. Pat. No. 5,474,918), *E. coli* FERM BP-3519 and FERM BP-3520 (U.S. Pat. No. 5,376,538), *E. coli* MG442 (Gusyatiner M. et al., Genetika (in Russian), 1978: 14, 947-956), *E. coli* VL643 and VL2055 (EP 1149911 A), and the like.

The strain TDH-6 is deficient in the thrC gene, as well as being sucrose-assimilative, and the ilvA gene has a leaky mutation. This strain also has a mutation in the rhtA gene, which imparts resistance to high concentrations of threonine or homoserine. The strain B-3996 contains the plasmid pVIC40 which was obtained by inserting a thrA*BC operon which includes a mutant thrA gene into a RSF1010-derived vector. This mutant thrA gene encodes aspartokinase homoserine dehydrogenase I which has substantially desensitized feedback inhibition by threonine (U.S. Pat. No. 5,175, 107). The strain B-3996 was deposited on Nov. 19, 1987 in the All-Union Scientific Center of Antibiotics (Russian Federation, 117105 Moscow, Nagatinskaya Street 3-A) under the accession number RIA 1867. The strain was also deposited in the Russian National Collection of Industrial Microorganisms (VKPM) (Russian Federation, 117545 Moscow, 1$^{st}$ Dorozhny proezd, 1) on Apr. 7, 1987 under the accession number B-3996.

*E. coli* VKPM B-5318 (EP0593792B1) can also be used as a parent strain for deriving L-threonine-producing bacteria. The strain B-5318 is prototrophic with regard to isoleucine, and a temperature-sensitive lambda-phage C1 repressor and PR promoter replaces the regulatory region of the threonine operon in plasmid pVIC40. The strain VKPM B-5318 was deposited in the Russian National Collection of Industrial Microorganisms (VKPM) on May 3, 1990 under accession number of VKPM B-5318.

The bacterium can be additionally modified to enhance expression of one or more of the following genes (RU2275424):

the mutant thrA gene which encodes aspartokinase I and homoserine dehydrogenase I resistant to feedback inhibition by L-threonine;
the thrB gene which encodes homoserine kinase;
the thrC gene which encodes threonine synthase;
the rhtA gene which encodes a protein of the threonine and homoserine efflux system (an inner membrane transporter);
the asd gene which encodes aspartate-f3-semialdehyde dehydrogenase; and
the aspC gene which encodes aspartate aminotransferase.

The thrA gene which encodes aspartokinase I and homoserine dehydrogenase I of *E. coli* has been elucidated (KEGG entry No. b0002; GenBank accession No. NC_000913.2; nucleotide positions: 337 to 2,799; Gene ID: 945803). The thrA gene is located between the thrL and thrB genes on the chromosome of *E. coli* K-12.

The thrB gene which encodes homoserine kinase of *E. coli* has been elucidated (KEGG entry No. b0003; GenBank accession No. NC_000913.2; nucleotide positions: 2,801 to 3,733; Gene ID: 947498). The thrB gene is located between the thrA and thrC genes on the chromosome of *E. coli* K-12.

The thrC gene which encodes threonine synthase of *E. coli* has been elucidated (KEGG entry No. b0004; GenBank accession No. NC_000913.2; nucleotide positions: 3,734 to 5,020; Gene ID: 945198). The thrC gene is located between the thrB and yaaX genes on the chromosome of *E. coli* K-12. All three genes function as a single threonine operon thrABC. To enhance expression of the threonine operon, the attenuator region which affects the transcription is desirably removed from the operon (WO2005049808A1, WO2003097839A1).

The mutant thrA gene which encodes aspartokinase I and homoserine dehydrogenase I resistant to feedback inhibition by L-threonine, as well as, the thrB and thrC genes can be obtained as one operon from well-known plasmid pVIC40 which is present in the threonine producing *E. coli* strain VKPM B-3996. Plasmid pVIC40 is described in detail in U.S. Pat. No. 5,705,371.

The rhtA gene which encodes a protein of the threonine and homoserine efflux system (an inner membrane transporter) of *E. coli* has been elucidated (KEGG entry No. b0813; GenBank accession No. NC_000913.2; nucleotide positions: 848,433 to 849,320, complement; Gene ID: 947045). The rhtA gene is located between the dps and ompX genes on the chromosome of *E. coli* K-12 close to the glnHPQ operon, which encodes components of the glutamine transport system. The rhtA gene is identical to ybiF gene (KEGG entry No. B0813).

The asd gene which encodes aspartate-β-semialdehyde dehydrogenase of *E. coli* has been elucidated (KEGG entry No. b3433; GenBank accession No. NC_000913.2; nucleotide positions: 3,571,798 to 3,572,901, complement; Gene ID: 947939). The asd gene is located between the glgB and gntU gene on the same strand (yhgN gene on the opposite strand) on the chromosome of *E. coli* K-12.

Also, the aspC gene which encodes aspartate aminotransferase of *E. coli* has been elucidated (KEGG entry No. b0928; GenBank accession No. NC_000913.2; nucleotide positions: 983,742 to 984,932, complement; Gene ID: 945553).

The aspC gene is located between the ycbL gene on the opposite strand and the ompF gene on the same strand on the chromosome of *E. coli* K-12.

Furthermore, L-threoine-producing bacteria may have reduced or no activity of an enzyme that negatively acts on L-threonine synthesis or accumulation. Examples of such enzymes include threonine dehydrogenase encoded by the tdh gene, and so forth (WO2009022754A1).

*E. coli* B-3996Δ(ordL-narW) strain can also be used as a parent strain for deriving L-threonine-producing bacteria. The strain B-3996Δ(ordL-narW) was named as AG7843 and deposited in the Russian National Collection of Industrial Microorganisms (VKPM) (Russia, 117545 Moscow, 1 Dorozhny proezd 1) on May 21, 2010 under the accession number B-10647, and the national deposit form was then converted to the international deposit form under the provisions of Budapest Treaty on Jul. 19, 2012.

L-Lysine-Producing Bacteria

L-Lysine-producing bacteria and methods for constructing them are exemplified below.

Examples of strains having L-lysine-producing ability include, for example, L-lysine analogue-resistant strains and metabolic regulation mutant strains. Examples of L-lysine analogues include, but are not limited to, oxalysine, lysine hydroxamate, S-(2-aminoethyl)-L-cysteine (AEC), γ-methyllysine, α-chlorocaprolactam, and so forth. Mutant strains having resistance to these lysine analogues can be obtained by subjecting a bacterium belonging to the family Enterobacteriaceae to a conventional artificial mutagenesis treatment. Specific examples of L-lysine-producing bacteria include *E. coli* AJ11442 (FERM BP-1543, NRRL B-12185, see Japanese Patent Laid-open No. 56-18596 and U.S. Pat. No. 4,346,170), *E. coli* VL611 strain (Japanese Patent Laid-open No. 2000-189180), and so forth. As an L-lysine-producing *E. coli*, the WC196 strain may also be used (see International Patent Publication WO96/17930).

Furthermore, an L-lysine-producing bacterium can also be constructed by increasing activity of an L-lysine biosynthesis system enzyme. The activity of such an enzyme can be increased by increasing the copy number of the gene encoding the enzyme in the cells, or by modifying an expression control sequence thereof. Increasing the copy number of a gene encoding an enzyme of the L-lysine biosynthesis system and modifying an expression control sequence thereof can be attained by the same method as for the gltP and gltS genes described later.

Examples of genes encoding L-lysine biosynthetic enzymes include genes encoding enzymes of the diaminopimelate pathway, such as dihydrodipicolinate synthase gene (dapA), aspartokinase gene (lysC), dihydrodipicolinate reductase gene (dapB), diaminopimelate decarboxylase gene (lysA), diaminopimelate dehydrogenase gene (ddh) (WO96/40934 for all the foregoing genes), phosphoenolpyrvate carboxylase gene (ppc) (Japanese Patent Laid-open No. 60-87788), aspartate aminotransferase gene (aspC) (Japanese Patent Publication (Kokoku) No. 6-102028), and aspartate semialdehyde dehydrogenase gene (asd) (WO00/61723), and genes encoding enzymes of the aminoadipic acid pathway such as homoaconitrate hydratase gene (Japanese Patent Laid-open No. 2000-157276). In addition, the bacterial strain may have an increased level of expression of the gene involved in energy efficiency (cyo) (European Patent Laid-open No. 1170376), the gene encoding nicotinamide nucleotide transhydrogenase (pntAB) (U.S. Pat. No. 5,830,716), the ybjE gene encoding a protein having L-lysine excretion activity (WO2005/073390), the gene encoding glutamate dehydrogenase (gdhA) (Gene 23:199-209, 1983), or any random combination of these. Abbreviations for the genes are shown in parentheses. Among the aforementioned genes, the ybjE gene is one example.

It is known that the wild-type dihydrodipicolinate synthase derived from *E. coli* is subject to feedback inhibition by L-lysine, and it is known that the wild-type aspartokinase derived from *E. coli* is subject to suppression and feedback inhibition by L-lysine. Therefore, when the dapA gene and lysC gene are used, genes encoding mutant enzymes desensitized to the feedback inhibition by L-lysine can be used. Examples of DNA encoding a mutant dihydrodipicolinate synthetase desensitized to feedback inhibition by L-lysine include a DNA encoding such a protein having an amino acid sequence in which the histidine residue at the position 118 is replaced by tyrosine residue. Examples of DNA encoding a mutant aspartokinase desensitized to feedback inhibition by L-lysine include a DNA encoding an AKIII protein having an amino acid sequence in which the threonine residue at the position 352, the glycine residue at the position 323, and the methionine residue at the position 318 are replaced by isoleucine, asparagine, and isoleucine residues, respectively (for these mutants, see U.S. Pat. Nos. 5,661,012 and 6,040,160). Such mutant DNAs can be obtained by site-specific mutagenesis using PCR, or the like.

Wide host-range plasmids RSFD80, pCAB1 and pCABD2 are known to contain a mutant dapA gene encoding a mutant dihydrodipicolinate synthase and a mutant lysC gene encoding a mutant aspartokinase (U.S. Pat. No. 6,040,160). *E. coli* JM109 strain transformed with this plasmid was named AJ12396 (U.S. Pat. No. 6,040,160), and the strain was deposited at the National Institute of Bioscience and Human-Technology, Agency of Industrial Science and Technology, Ministry of International Trade and Industry (currently National Institute of Advanced Industrial Science and Technology, International Patent Organism Depositary) on Oct. 28, 1993 and assigned an accession number of FERM P-13936, and the deposit was then converted to an international deposit under the provisions of Budapest Treaty on Nov. 1, 1994 and assigned an accession number of FERM BP-4859. RSFD80 can be obtained from the AJ12396 strain by a conventional method.

Furthermore, L-amino acid-producing bacteria may have reduced or no activity of an enzyme that catalyzes a reaction which causes a branching off from the L-amino acid biosynthesis pathway and results in the production of another compound. Also, the bacteria may have reduced or no activity of an enzyme that negatively acts on L-amino acid synthesis or accumulation. Examples of such enzymes involved in L-lysine production include homoserine dehydrogenase, lysine decarboxylase (cadA, ldcC), malic enzyme, and so forth, and strains in which activities of these enzymes are decreased or deleted are disclosed in WO95/23864, WO96/17930, WO2005/010175, and so forth.

Expression of both the cadA and ldcC genes encoding lysine decarboxylase can be decreased in order to decrease or delete the lysine decarboxylase activity. Expression of the both genes can be decreased by, for example, the method described in WO2006/078039.

In order to reduce or eliminate activities of the enzymes, a mutation may be introduced into the genes encoding the enzymes on the genome by a known mutagenesis method or gene recombination technique so that intracellular activities of the enzymes are reduced or eliminated. Such introduction of a mutation can be achieved by, for example, using genetic recombination to eliminate the genes encoding the enzymes on the genome or to modify an expression control sequence such as a promoter or the Shine-Dalgarno (SD) sequence. A mutation can also be introduced to impart an amino acid substitution (missense mutation), a stop codon (nonsense mutation), or a frame shift mutation which results in the addition or deletion of one or two nucleotides into the regions encoding the enzymes on the genome, or partially or totally deleting the genes (J. Biol. Chem., 272:8611-8617, 1997).

The enzymatic activities can also be decreased or eliminated by constructing a gene encoding a mutant enzyme, in which the coding region is entirely or partially deleted, and substituting it for a normal gene on the genome by homologous recombination or the like, or by introducing a transposon or IS factor into the gene. For example, in order to introduce a mutation that decreases or eliminates the activities of the above-mentioned enzymes by genetic recombination, the following methods can be used. A mutant gene is prepared by modifying part of the sequence of an objective gene so that it does not encode an enzyme that can function normally, and then a bacterium belonging to the family Enterobacteriaceae can be transformed with a DNA containing the mutant gene to cause recombination of a corresponding gene on the genome with the mutant gene to substitute the mutant gene for the objective gene on the genome. Examples of such gene substitution using homologous recombination include methods of using a linear DNA such as the method called Red-driven integration (Datsenko K. A. and Wanner B. L., *Proc. Natl. Acad. Sci. USA*, 2000, 97: 6640-6645), and the method utilizing the Red-driven integration in combination with an excisive system derived from λ phage (Cho E. H. et al., *J. Bacteriol.*, 2002, 184: 5200-5203) (refer to WO2005/010175), a method of using a plasmid containing a temperature sensitive replication origin (U.S. Pat. No. 6,303,383, Japanese Patent Laid-open No. 05-007491), and so forth. Furthermore, such site-specific mutagenesis based on gene substitution using homologous recombination as described above can also be performed by using a plasmid that is unable to replicate in a host.

Examples of L-lysine-producing bacteria include the *E. coli* WC196ΔcadAΔldcC/pCABD2 strain (WO2006/078039). The strain was constructed by introducing the plasmid pCABD2 containing lysine biosynthesis genes (U.S. Pat. No. 6,040,160) into the WC196 strain having disrupted cadA and ldcC genes, which encode lysine decarboxylase. The WC196 strain was bred from the W3110 strain, which was derived from *E. coli* K-12, by replacing the wild-type lysC gene on the chromosome of the W3110 strain with a mutant lysC gene encoding a mutant aspartokinase III in which threonine at position 352 was replaced with isoleucine, resulting in desensitization of the feedback inhibition thereof by L-lysine (U.S. Pat. No. 5,661,012), and conferring AEC resistance to the resulting strain (U.S. Pat. No. 5,827,698). The WC196 strain was designated *E. coli* AJ13069, deposited at the National Institute of Bioscience and Human-Technology, Agency of Industrial Science and Technology (currently the independent administrative agency, National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Dec. 6, 1994, and assigned an accession number of FERM P-14690. Then, it was converted to an international deposit under the provisions of the Budapest Treaty on Sep. 29, 1995, and assigned an accession number of FERM BP-5252 (U.S. Pat. No. 5,827,698). The WC196ΔcadAΔldcC strain itself is also an exemplary L-lysine-producing bacterium. The WC196ΔcadAΔldcC was designated AJ110692, and deposited at the National Institute of Bioscience and Human-Technology, Agency of Industrial Science and Technology (currently the independent administrative agency, National Institute of Advanced Industrial Science and Technology, International Patent Organism Depositary (Tsukuba Central 6, 1-1, Higashi 1-Chome, Tsukuba-shi, Ibaraki-ken, 305-8566, Japan) on Oct. 7, 2008 as an international deposit and assigned an accession number of FERM BP-11027.

The plasmid pCABD2 contains a mutant dapA gene derived from *E. coli* that encodes a dihydrodipicolinate synthase (DDPS) having a mutation for desensitization to the feedback inhibition by L-lysine, a mutant lysC gene derived from *E. coli* that encodes aspartokinase III having a mutation for desensitization to the feedback inhibition by L-lysine, the dapB gene derived from *E. coli* that encodes dihydrodipicolinate reductase, and the ddh gene derived from *Brevibacterium lactofermentum* that encodes diaminopimelate dehydrogenase.

L-Cysteine-Producing Bacteria

Examples of parent strains for deriving L-cysteine-producing bacteria include, but are not limited to, strains belonging to the genus *Escherichia*, such as *E. coli* JM15 which is transformed with different cysE alleles coding for feedback-resistant serine acetyltransferases (U.S. Pat. No. 6,218,168, Russian patent application 2003121601); *E. coli* W3110 having over-expressed genes which encode proteins suitable for secreting substances toxic for cells (U.S. Pat. No. 5,972,663); *E. coli* strains having lowered cysteine desulfohydrase activity (JP11155571A2); *E. coli* W3110 with increased activity of a positive transcriptional regulator for cysteine regulon encoded by the cysB gene (WO0127307A1), and the like.

L-Leucine-Producing Bacteria

Examples of parent strains for deriving L-leucine-producing bacteria include, but are not limited to, strains belonging to the genus *Escherichia*, such as *E. coli* strains resistant to leucine (for example, the strain 57 (VKPM B-7386, U.S. Pat. No. 6,124,121)) or leucine analogs including β-2-thienylalanine, 3-hydroxyleucine, 4-azaleucine, 5,5,5-trifluoroleucine (JP 62-34397 B and JP 8-70879 A); *E. coli* strains obtained by the gene engineering method described in WO96/06926; *E. coli* H-9068 (JP 8-70879 A), and the like.

The bacterium may be improved by enhancing the expression of one or more genes involved in L-leucine biosynthesis. Examples include genes of the leuABCD operon, which can be represented by a mutant leuA gene coding for isopropylmalate synthase freed from feedback inhibition by L-leucine (U.S. Pat. No. 6,403,342). In addition, the bacterium can be improved by enhancing the expression of one or more genes coding for proteins which excrete L-amino acid from the bacterial cell. Examples of such genes include the b2682 and b2683 genes (ygaZH genes) (EP 1239041 A2).

L-Histidine-Producing Bacteria

Examples of parent strains for deriving L-histidine-producing bacteria include, but are not limited to, strains belonging to the genus *Escherichia*, such as *E. coli* strain 24 (VKPM B-5945, RU2003677); *E. coli* strain 80 (VKPM B-7270, RU2119536); *E. coli* NRRL B-12116-B12121 (U.S. Pat. No. 4,388,405); *E. coli* H-9342 (FERM BP-6675) and H-9343 (FERM BP-6676) (U.S. Pat. No. 6,344,347); *E. coli* H-9341 (FERM BP-6674) (EP1085087); *E. coli* AI80/pFM201 (U.S. Pat. No. 6,258,554) and the like.

Examples of parent strains for deriving L-histidine-producing bacteria also include strains in which expression of one or more genes encoding an L-histidine biosynthetic enzyme are enhanced. Examples of such genes include genes encoding ATP phosphoribosyltransferase (hisG), phosphoribosyl AMP cyclohydrolase (hisI), phosphoribosyl-ATP pyrophosphohydrolase (hisIE), phosphoribosylformimino-5-aminoimidazole carboxamide ribotide isomerase (hisA), amidotransferase (hisH), histidinol phosphate aminotransferase (hisC), histidinol phosphatase (hisB), histidinol dehydrogenase (hisD), and so forth.

It is known that the L-histidine biosynthetic enzymes encoded by hisG and hisBHAFI are inhibited by L-histidine, and therefore an L-histidine-producing ability can also be efficiently enhanced by introducing a mutation conferring resistance to the feedback inhibition into ATP phosphoribosyltransferase (Russian Patent Nos. 2003677 and 2119536).

Specific examples of strains having an L-histidine-producing ability include *E. coli* FERM-P 5038 and 5048 which have been introduced with a vector carrying a DNA encoding an L-histidine-biosynthetic enzyme (JP 56-005099 A), *E. coli* strains introduced with rht, a gene for an amino acid-export (EP1016710A), *E. coli* 80 strain imparted with sulfaguanidine, DL-1,2,4-triazole-3-alanine, and streptomycin-resistance (VKPM B-7270, Russian Patent No. 2119536), and so forth.

L-Glutamic Acid-Producing Bacteria

Examples of parent strains for deriving L-glutamic acid-producing bacteria include, but are not limited to, strains belonging to the genus *Escherichia*, such as *E. coli* VL334thrC$^+$ (EP 1172433). *E. coli* VL334 (VKPM B-1641) is an L-isoleucine and L-threonine auxotrophic strain having mutations in thrC and ilvA genes (U.S. Pat. No. 4,278,765). A wild-type allele of the thrC gene was transferred by the method of general transduction using a bacteriophage P1 grown on the wild-type *E. coli* strain K12 (VKPM B-7) cells. As a result, an L-isoleucine auxotrophic strain VL334thrC$^+$ (VKPM B-8961), which is able to produce L-glutamic acid, was obtained.

Examples of parent strains for deriving the L-glutamic acid-producing bacteria include, but are not limited to, strains in which expression of one or more genes encoding an L-glutamic acid biosynthetic enzyme are enhanced. Examples of such genes include genes encoding glutamate dehydrogenase (gdhA), glutamine synthetase (glnA), glutamate synthetase (gltAB), isocitrate dehydrogenase (icdA), aconitate hydratase (acnA, acnB), citrate synthase (gltA), phosphoenolpyruvate carboxylase (ppc), pyruvate carboxylase (pyc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phophate dehydrogenase (gapA), triose phosphate isomerase (tpiA), fructose bisphosphate aldolase (fbp), phosphofructokinase (pfkA, pfkB), and glucose phosphate isomerase (pgi).

Examples of strains modified so that expression of the citrate synthetase gene, the phosphoenolpyruvate carboxylase gene, and/or the glutamate dehydrogenase gene is/are enhanced include those disclosed in EP1078989B1, EP955368B1, and EP952221B1.

Examples of parent strains for deriving the L-glutamic acid-producing bacteria also include strains having decreased or eliminated activity of an enzyme that catalyzes synthesis of a compound other than L-glutamic acid by branching off from an L-glutamic acid biosynthesis pathway. Examples of such enzymes include isocitrate lyase (aceA), α-ketoglutarate dehydrogenase (sucA), phosphotransacetylase (pta), acetate kinase (ack), acetohydroxy acid synthase (ilvG), acetolactate synthase (ilvI), formate acetyltransferase (pfl), lactate dehydrogenase (ldh), and glutamate decarboxylase (gadAB). Bacteria belonging to the genus *Escherichia* deficient in the α-ketoglutarate dehydrogenase activity or having a reduced á-ketoglutarate dehydrogenase activity and methods for obtaining them are described in U.S. Pat. Nos. 5,378,616 and 5,573,945. Specifically, these strains include the following:

*E. coli* W3110sucA::Km$^R$
*E. coli* AJ12624 (FERM BP-3853)
*E. coli* AJ12628 (FERM BP-3854)
*E. coli* AJ12949 (FERM BP-4881)

*E. coli* W3110sucA::Km$^R$ is a strain obtained by disrupting the α-ketoglutarate dehydrogenase gene (hereinafter referred to as "sucA gene") of *E. coli* W3110. This strain is completely deficient in α-ketoglutarate dehydrogenase.

Other examples of L-glutamic acid-producing bacterium include those which belong to the genus *Escherichia* and have resistance to an aspartic acid antimetabolite. These strains can also be deficient in the α-ketoglutarate dehydrogenase activity and include, for example, *E. coli* AJ13199 (FERM BP-5807) (U.S. Pat. No. 5,908,768), FFRM P-12379, which additionally has a low L-glutamic acid decomposing ability (U.S. Pat. No. 5,393,671); AJ13138 (FERM BP-5565) (U.S. Pat. No. 6,110,714), and the like.

Examples of L-glutamic acid-producing bacteria include mutant strains belonging to the genus *Pantoea* which are deficient in α-ketoglutarate dehydrogenase activity or have a decreased α-ketoglutarate dehydrogenase activity, and can be obtained as described above. Such strains include *Pantoea ananatis* AJ13356. (U.S. Pat. No. 6,331,419). *Pantoea ananatis* AJ13356 was deposited at the National Institute of Bioscience and Human-Technology, Agency of Industrial Science and Technology, Ministry of International Trade and Industry (currently, National Institute of Advanced Industrial Science and Technology, International Patent Organism Depositary, Central 6, 1-1, Higashi 1-Chome, Tsukuba-shi, Ibaraki-ken, 305-8566, Japan) on Feb. 19, 1998 under an accession number of FERM P-16645. It was then converted to an international deposit under the provisions of Budapest Treaty on Jan. 11, 1999 and received an accession number of FERM BP-6615. *Pantoea ananatis* AJ13356 is deficient in the α-ketoglutarate dehydrogenase activity as a result of disruption of the αKGDH-E1 subunit gene (sucA). The above strain was identified as *Enterobacter agglomerans* when it was isolated and deposited as the *Enterobacter agglomerans* AJ13356. However, it was recently re-classified as *Pantoea ananatis* on the basis of nucleotide sequencing of 16S rRNA and so forth. Although AJ13356 was deposited at the aforementioned depository as *Enterobacter agglomerans*, for the purposes of this specification, they are described as *Pantoea ananatis*.

L-Phenylalanine-Producing Bacteria

Examples of parent strains for deriving L-phenylalanine-producing bacteria include, but are not limited to, strains belonging to the genus *Escherichia*, such as *E. coli* AJ12739 (tyrA::Tn10, tyrR) (VKPM B-8197); *E. coli* HW1089 (ATCC 55371) harboring the mutant pheA34 gene (U.S. Pat. No. 5,354,672); *E. coli* MWEC101-b (KR8903681); *E. coli* NRRL B-12141, NRRL B-12145, NRRL B-12146 and NRRL B-12147 (U.S. Pat. No. 4,407,952). Also, as a parent strain, *E. coli* K-12 [W3110 (tyrA)/pPHAB (FERM BP-3566), *E. coli* K-12 [W3110 (tyrA)/pPHAD] (FERM BP-12659), *E. coli* K-12 [W3110 (tyrA)/pPHATerm] (FERM BP-12662) and *E. coli* K-12 [W3110 (tyrA)/pBR-aroG4, pACMAB] named as AJ 12604 (FERM BP-3579) may be used (EP 488424 B1). Furthermore, L-phenylalanine producing bacteria belonging to the genus *Escherichia* with an enhanced activity of the protein encoded by the yedA gene or the yddG gene may also be used (U.S. patent applications 2003/0148473 A1 and 2003/0157667 A1).

L-Tryptophan-Producing Bacteria

Examples of parent strains for deriving the L-tryptophan-producing bacteria include, but are not limited to, strains belonging to the genus *Escherichia*, such as *E. coli* JP4735/ pMU3028 (DSM10122) and JP6015/pMU91 (DSM10123) deficient in the tryptophanyl-tRNA synthetase encoded by mutant trpS gene (U.S. Pat. No. 5,756,345); *E. coli* SV164 (pGH5) having a serA allele encoding phosphoglycerate dehydrogenase free from feedback inhibition by serine and a trpE allele encoding anthranilate synthase free from feedback inhibition by tryptophan (U.S. Pat. No. 6,180,373); *E. coli* AGX17 (pGX44) (NRRL B-12263) and AGX6(pGX50)aroP (NRRL B-12264) deficient in the enzyme tryptophanase (U.S. Pat. No. 4,371,614); *E. coli* AGX17/pGX50,pACKG4-pps in which a phosphoenolpyruvate-producing ability is enhanced (WO9708333, U.S. Pat. No. 6,319,696), and the like may be used. L-tryptophan-producing bacteria belonging to the genus *Escherichia* with an enhanced activity of the identified protein encoded by the yedA gene or the yddG gene may also be used (U.S. patent applications 2003/0148473 A1 and 2003/0157667 A1).

Examples of parent strains for deriving the L-tryptophan-producing bacteria also include strains in which one or more activities of the enzymes selected from anthranilate synthase, phosphoglycerate dehydrogenase, and tryptophan synthase are enhanced. The anthranilate synthase and phosphoglycerate dehydrogenase are both subject to feedback inhibition by L-tryptophan and L-serine, so that a mutation desensitizing the feedback inhibition may be introduced into these enzymes. Specific examples of strains having such a mutation include an *E. coli* SV164 which harbors desensitized anthranilate synthase and a transformant strain obtained by introducing into the *E. coli* SV164 the plasmid pGH5 (WO 94/08031), which contains a mutant serA gene encoding feedback-desensitized phosphoglycerate dehydrogenase.

Examples of parent strains for deriving the L-tryptophan-producing bacteria also include strains into which the tryptophan operon which contains a gene encoding desensitized anthranilate synthase has been introduced (JP 57-71397 A, JP 62-244382 A, U.S. Pat. No. 4,371,614). Moreover, L-tryptophan-producing ability may be imparted by enhancing expression of a gene which encodes tryptophan synthase, among tryptophan operons (trpBA). The tryptophan synthase consists of α and β subunits which are encoded by the trpA and trpB genes, respectively. In addition, L-tryptophan-producing ability may be improved by enhancing expression of the isocitrate lyase-malate synthase operon (WO2005/103275).

L-Proline-Producing Bacteria

Examples of parent strains for deriving L-proline-producing bacteria include, but are not limited to, strains belonging to the genus *Escherichia*, such as *E. coli* 702ilvA (VKPM B-8012) which is deficient in the ilvA gene and is able to produce L-proline (EP 1172433). The bacterium can be improved by enhancing the expression of one or more genes involved in L-proline biosynthesis. Examples of such genes for L-proline producing bacteria include the proB gene coding for glutamate kinase of which feedback inhibition by L-proline is desensitized (DE Patent 3127361). In addition, the bacterium can be improved by enhancing the expression of one or more genes coding for proteins excreting L-amino acid from bacterial cell. Such genes are exemplified by b2682 and b2683 genes (ygaZH genes) (EP1239041 A2).

Examples of bacteria belonging to the genus *Escherichia*, which have an activity to produce L-proline include the following *E. coli* strains: NRRL B-12403 and NRRL B-12404 (GB Patent 2075056), VKPM B-8012 (Russian patent application 2000124295), plasmid mutants described in DE Patent 3127361, plasmid mutants described by Bloom F. R. et al (The 15$^{th}$ Miami winter symposium, 1983, p. 34), and the like.

L-Arginine-Producing Bacteria

Examples of parent strains for deriving L-arginine-producing bacteria include, but are not limited to, strains belonging to the genus *Escherichia*, such as *E. coli* strain 237 (VKPM B-7925) (U.S. Patent Application 2002/058315 A1) and its derivative strains harboring mutant N-acetylglutamate synthase (Russian Patent Application No. 2001112869), *E. coli* strain 382 (VKPM B-7926) (EP1170358A1), an arginine-producing strain into which argA gene encoding N-acetylglutamate synthetase is introduced therein (EP1170361A1), and the like.

Examples of parent strains for deriving L-arginine producing bacteria also include strains in which expression of one or more genes encoding an L-arginine biosynthetic enzyme are enhanced. Examples of such genes include genes encoding N-acetylglutamyl phosphate reductase (argC), ornithine acetyl transferase (argJ), N-acetylglutamate kinase (argB), acetylornithine transaminase (argD), ornithine carbamoyl transferase (argF), argininosuccinic acid synthetase (argG), argininosuccinic acid lyase (argH), and carbamoyl phosphate synthetase (carAB).

L-Valine-Producing Bacteria

Examples of parent strains for deriving L-valine-producing bacteria include, but are not limited to, strains which have been modified to overexpress the ilvGMEDA operon (U.S. Pat. No. 5,998,178). It is desirable to remove the region of the ilvGMEDA operon which is required for attenuation so that expression of the operon is not attenuated by L-valine that is produced. Furthermore, the ilvA gene in the operon is desirably disrupted so that threonine deaminase activity is decreased.

Examples of parent strains for deriving L-valine-producing bacteria include also include mutants having a mutation of amino-acyl t-RNA synthetase (U.S. Pat. No. 5,658,766). For example, *E. coli* VL1970, which has a mutation in the ileS gene encoding isoleucine tRNA synthetase, can be used. *E. coli* VL1970 has been deposited in the Russian National Collection of Industrial Microorganisms (VKPM) (Russian Federation, 117545 Moscow, 1$^{st}$ Dorozhny Proezd, 1) on Jun. 24, 1988 under accession number VKPM B-4411. Furthermore, mutants requiring lipoic acid for growth and/or lacking H$^{+}$-ATPase can also be used as parent strains (WO96/06926).

L-Isoleucine-Producing Bacteria

Examples of parent strains for deriving L-isoleucine producing bacteria include, but are not limited to, mutants having resistance to 6-dimethylaminopurine (JP 5-304969 A), mutants having resistance to an isoleucine analogue such as thiaisoleucine and isoleucine hydroxamate, and mutants additionally having resistance to DL-ethionine and/or arginine hydroxamate (JP 5-130882 A). In addition, recombinant strains transformed with genes encoding proteins involved in L-isoleucine biosynthesis, such as threonine deaminase and acetohydroxate synthase, can also be used as parent strains (JP 2-458 A, FR 0356739, and U.S. Pat. No. 5,998,178).

2. Method According to the Present Invention

The method of the present invention is a method for producing L-amino acid by cultivating the bacterium of the present invention in a culture medium to produce and excrete the L-amino acid into the medium, and collecting the L-amino acid from the medium.

The cultivation, collection and purification of L-amino acid from the medium and the like may be performed in a manner similar to conventional fermentation methods wherein an amino acid is produced using a bacterium.

A medium used for culture may be either a synthetic or natural medium, so long as the medium includes a carbon source and a nitrogen source and minerals and, if necessary, appropriate amounts of nutrients which the bacterium requires for growth. The carbon source may include various carbohydrates such as glucose and sucrose, and various organic acids. Depending on the mode of assimilation of the chosen microorganism, alcohol, including ethanol and glycerol, may be used. As the nitrogen source, various ammonium salts such as ammonia and ammonium sulfate, other nitrogen compounds such as amines, a natural nitrogen source such as peptone, soybean-hydrolysate and digested fermentative microorganism can be used. As minerals, potassium monophosphate, magnesium sulfate, sodium chloride, ferrous sulfate, manganese sulfate, calcium chloride, and the like can be used. As vitamins, thiamine, yeast extract, and the like, can be used.

The cultivation can be performed under aerobic conditions, such as a shaking culture and a stirring culture with aeration, at a temperature of 20 to 40° C., or 30 to 38° C. The pH of the culture is usually between 5 and 9, or between 6.5 and 7.2. The pH of the culture can be adjusted with ammonia, calcium carbonate, various acids, various bases, and buffers. Usually, 1 to 5-day cultivation leads to accumulation of the target L-amino acid in the liquid medium.

After cultivation, solids such as cells can be removed from the liquid medium by centrifugation or membrane filtration, and then the L-amino acid can be collected and purified by concentration, and/or crystallization methods, and/or various chromatographic methods.

The collected L-amino acid composition can contain bacterial cells, medium components, moisture, and by-product metabolites of the microorganism in addition to the L-amino acid. Purity of the collected L-amino acid can be, for example, 50% or higher, 85% or higher, or even 95% or higher (U.S. Pat. No. 5,431,933, Japanese Patent Publication No. 1-214636, U.S. Pat. Nos. 4,956,471, 4,777,051, 4,946,654, 5,840,358, 6,238,714, U.S. Patent Published Application No. 2005/0025878).

Furthermore, when the L-amino acid precipitates in the medium, it can be collected by centrifugation, filtration or the like. The L-amino acid precipitated in the medium and the L-amino acid dissolved in the medium may be isolated together after the L-amino acid dissolved in the medium is crystallized.

EXAMPLES

The present invention will be more precisely explained below with reference to the following non-limiting Examples.

Example 1

Construction of the *E. coli* MG1655::Δtdh,rhtA*, $P_{tac7}$flhDC Strain

The *E. coli* strain MG1655::Δtdh,rhtA*,$P_{tac7}$flhDC strain was obtained by substitution of the native promoter region of the flhDC operon in the strain MG1655::Δtdh,rhtA* with the promoter $P_{tac7}$ (FIG. 1), which is derived from the $P_{tac}$ promoter. The $P_{tac7}$ promoter carries the deletion of C-nucleotide (the $23^{rd}$ position upstream to ATG codon) in LacI-binding site region to abolish LacI-dependent repression.

To substitute the native promoter region of the flhDC operon, a DNA fragment carrying the $P_{tac7}$ promoter and kanamycin resistance marker ($Km^R$) encoded by kan gene was integrated in the place of the native promoter region on the chromosome of the *E. coli* MG1655::Δtdh,rhtA* strain by the method described by Datsenko K. A. and Wanner B. L. (*Proc. Natl. Acad. Sci. USA*, 2000, 97:6640-6645), which is also called as a "Red-mediated integration" and/or "Red-driven integration". The strain MG1655::Δtdh,rhtA* was constructed as described in detail in the Russian Patent No. 2364628C2 and WO2009022754A1. The recombinant plasmid pKD46 (Datsenko K. A. and Wanner B. L., *Proc. Natl. Acad. Sci. USA*, 2000, 97:6640-6645) with the temperature-sensitive replicon was used as the donor of the phage λ-derived genes responsible for the Red-mediated recombination system. *E. coli* strain BW25113 containing the recombinant plasmid pKD46 can be obtained from the *E. coli* Genetic Stock Center, Yale University, New Haven, USA, the accession number is CGSC7630. After integration of the plasmid pKD46 into the *E. coli* MG1655::Δtdh,rhtA* strain, the strain MG1655::Δtdh,rhtA*/pKD46 was obtained.

The $P_{tac7}$ promoter fragment was obtained by PCR using the commercially available plasmid pKK223-3 ("Pharmacia") as a template and primers P1 (SEQ ID NO: 9) and P2 (SEQ ID NO: 10). Primer P1 contains 21 nucleotides homologous to the 5'-region of kan gene required for further joining with $P_{tac7}$ promoter. Primer P2 contains 40 nucleotides homologous to the 5'-region of flhD gene required for further integration into the bacterial chromosome. In addition, primer P2 has a deletion of C-nucleotide (the $23^{rd}$ position upstream to ATG codon) in LacI-binding site region.

The DNA fragment containing $Km^R$ marker encoded by kan gene was obtained by PCR using the commercially available plasmid pACYC177 (GenBank accession number X06402, "Fermentas", Lithuania) as the template and primers P3 (SEQ ID NO: 11) and P4 (SEQ ID NO: 12). Primer P3 contains 41 nucleotides homologous to the region located 188 bp upstream of the start codon of the flhD gene required for further integration into the bacterial chromosome. Primer P4 contains 21 nucleotides homologous to the 5'-region of $P_{tac7}$ promoter required for further joining with kan gene.

PCR was provided using the "GeneAmp PCR System 2700" thermal cycler (Applied Biosystems). The reaction mixture with total volume of 50 μl consisted of 5 μl of 10× PCR-buffer with 25 mM $MgCl_2$ ("Fermentas", Lithuania), 200 μM each of dNTP, 25 pmol each of the exploited primers and 1 U of Taq-polymerase ("Fermentas", Lithuania). Approximately 5 ng of the plasmid DNA was added into the reaction mixture as a template DNA for the PCR amplification. The temperature profile was the following: initial DNA denaturation for 5 min at 95° C. followed by 25 cycles of: denaturation at 95° C. for 30 sec, annealing at 54° C. for 30 sec and elongation at 72° C. for 20 sec for $P_{tac7}$ promoter or 50 sec for the kan gene; and the final elongation for 5 min at 72° C. Then, the amplified DNA fragment was purified by agarose gel-electrophoresis, extracted using "GenElute Spin Columns" ("Sigma", USA) and precipitated by ethanol.

The kan-$P_{tac7}$ DNA fragment was obtained by overlapping PCR using the two above-described DNA fragments and primers P1 (SEQ ID NO: 9) and P4 (SEQ ID NO: 12) to accomplish DNA fragments overlapping and amplification. The amplified kan-$P_{tac7}$ DNA fragment was purified by agarose gel-electrophoresis, extracted using "GenElute Spin Columns" ("Sigma", USA) and precipitated by ethanol. The obtained DNA fragment was used for electroporation and Red-mediated integration into the bacterial chromosome of the *E. coli* MG1655::Δtdh,rhtA*/pKD46.

The MG1655::Δtdh,rhtA*/pKD46 cells were grown overnight at 30° C. in the liquid LB-medium with addition of ampicillin (100 μg/ml), then diluted as 1:100 by the SOB-medium (yeast extract, 5 g/l; NaCl, 0.5 g/l; tryptone, 20 g/l; KCl, 2.5 mM; $MgCl_2$, 10 mM) with addition of ampicillin (100 μg/ml) and L-arabinose (10 mM) (Datsenko K. A. and Wanner B. L., *Proc. Natl. Acad. Sci. USA*, 2000, 97:6640-6645) and grown at 30° C. to reach the optical density of the bacterial culture $OD_{600}$ of 0.4-0.7. The grown cells from 10 ml of the bacterial culture medium were washed 3 times by ice-cold deionized water followed by suspending in 100 µl of water. 10 µl of DNA fragment (100 ng) dissolved in deionized water was added to the cell suspension. The electroporation was performed by "Bio-Rad" electroporator (USA) (No. 165-2098, version 2-89) according to the manufacturer's instructions.

Shocked cells were added to 1 ml of the SOC-medium (Sambrook et al, "Molecular Cloning A Laboratory Manual, $2^{nd}$ ed.", Cold Spring Harbor Laboratory Press (1989)), incubated 2 hours at 37° C., and then spread onto L-agar containing 20 µg/ml of kanamycin.

Colonies grown within 24 h were tested for the presence of $Km^R$ marker instead of the native promoter region of flhDC operon by PCR using primers P5 (SEQ ID NO: 13) and P6 (SEQ ID NO: 14). For this purpose, a freshly isolated colony was suspended in 20 µl water, and then 1 µl of obtained suspension was used for PCR. The temperature profile was the following: initial DNA denaturation for 10 min at 95° C. followed by 30 cycles of: denaturation at 95° C. for 30 sec, annealing at 55° C. for 30 sec and elongation at 72° C. for 1.5 min; and the final elongation for 5 min at 72° C. A few $Km^R$ colonies tested contained the desired 1460 bp DNA fragment, confirming presence of the $Km^R$ marker DNA instead of the 840 bp native promoter region of flhDC operon (FIG. 1). One of the obtained strains was cured from the thermosensitive plasmid pKD46 by culturing at 37° C. and the resulting strain was named as *E. coli* MG1655::Δtdh,rhtA*,$P_{tac7}$flhDC.

Example 2

Production of L-Threonine by the *E. coli* MG1655::Δtdh,rhtA*,$P_{tac7}$flhDC Strain The parent strain MG1655::Δtdh,rhtA* and MG1655::Δtdh,rhtA*,$P_{tac7}$flhDC were each transformed by plasmid pVIC40 (WO9004636A1, U.S. Pat. No. 5,705,371). Strains obtained were cultivated at 37° C. for 18 hours in a nutrient broth, then 0.1 ml of each of the obtained cultures was inoculated into 2 ml of fermentation medium in a 20×200 mm test-tube and cultivated at 37° C. for 24 and 48 hours on a rotary shaker.

The fermentation medium contained (g/l):

| | |
|---|---|
| Glucose | 40 |
| NaCl | 0.8 |
| $(NH_4)_2SO_4$ | 22 |
| $K_2HPO_4$ | 2.0 |
| $MgSO_4·7H_2O$ | 0.8 |
| $MnSO_4·5H_2O$ | 0.02 |
| $FeSO_4·7H_2O$ | 0.02 |
| Thiamine hydrochloride | 0.002 |
| Yeast extract | 1.0 |
| $CaCO_3$ | 30 |

Glucose and magnesium sulfate were sterilized separately. $CaCO_3$ was dry-heat sterilized at 180° C. for 2 hours. The pH was adjusted to 7.0. Antibiotic was introduced into the medium after sterilization.

After cultivation, the amount of L-threonine which had accumulated in the medium was determined by paper chromatography using the following mobile phase: butanol/acetic acid/water=4/1/1 (v/v). A solution (2%) of ninhydrin in acetone was used as a visualizing reagent. A spot containing L-threonine was cut off, L-threonine was eluted in 0.5% water solution of $CdCl_2$ and the amount of L-threonine was estimated spectrophotometrically at 540 nm.

The results of 20 independent test-tube fermentations (as average values) are shown in Table 1. As it can be seen from the Table 1, the modified *E. coli* MG1655::Δtdh,rhtA*, $P_{tac7}$flhDC (pVIC40) strain caused the higher amount of accumulation of L-threonine as compared with the parent *E. coli* MG1655Δtdh::rhtA (pVIC40) strain.

TABLE 1

| | 24 h | | | 48 h | | |
|---|---|---|---|---|---|---|
| Strain | $OD_{600}$ | Thr, g/l | $Thr/OD_{600}$, g/l | $OD_{600}$ | Thr, g/l | $Thr/OD_{600}$, g/l |
| MG1655::Δtdh, rhtA* (pVIC40) | 13.0 ± 0.2 | 5.0 ± 0.6 | 0.38 | 19.4 ± 1.0 | 4.7 ± 0.8 | 0.24 |
| MG1655::Δtdh, rhtA*, $P_{tac7}$flhDC (pVIC40) | 9.7 ± 0.3 | 7.7 ± 0.9 | 0.97 | 12.2 ± 0.3 | 7.7 ± 0.4 | 0.64 |

Example 3

Construction of the *E. coli* MG1655::Δtdh,rhtA*,ΔintB::yhjH,cat Strain

Figure 2:
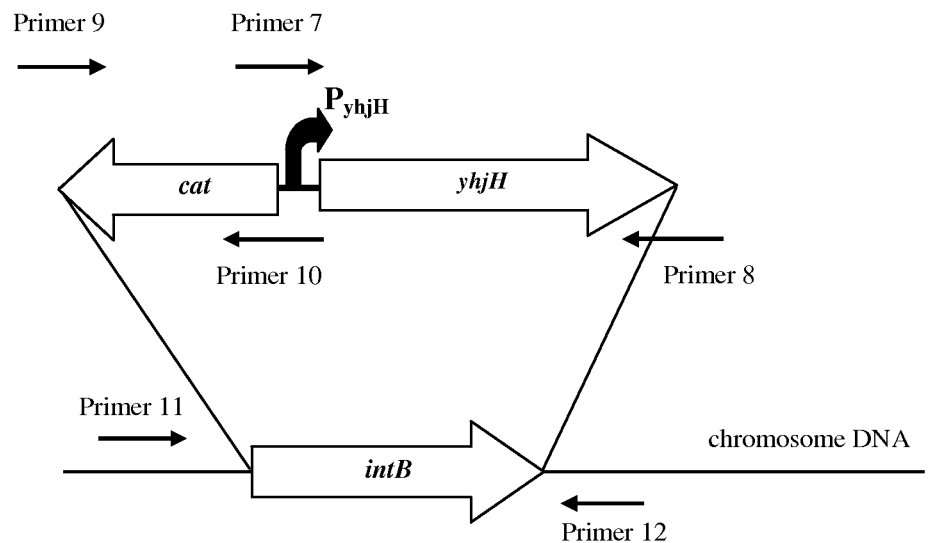
FIG. 2 is a scheme for the cat-P$_{yhjH}$-yhjH DNA fragment construction.

The *E. coli* strain MG1655::Δtdh,rhtA*,ΔintB::yhjH,cat strain was obtained by substitution of the native intB gene encoding integrase B in the strain MG1655::Δtdh,rhtA* with an additional copy of the yhjH gene under the control of its own promoter $P_{yhjH}$ (FIG. 2).

The DNA fragment carrying yhjH gene under control of its own promoter was integrated in the place of the native intB gene on the chromosome of the *E. coli* MG1655::Δtdh,rhtA* strain by the method described by Datsenko K. A. and Wanner B. L. (*Proc. Natl. Acad. Sci. USA*, 2000: 97, 6640-6645), which is also called as a "Red-mediated integration" and/or "Red-driven integration". The recombinant plasmid pKD46 (Datsenko K. A. and Wanner B. L., *Proc. Natl. Acad. Sci. USA*, 2000: 97, 6640-6645) with the thermosensitive replicon was used as the donor of the phage λ-derived genes responsible for the Red-mediated recombination system. *E. coli* strain BW25113 containing the recombinant plasmid pKD46 can be obtained from the *E. coli* Genetic Stock Center, Yale University, New Haven, USA, the accession number is CGSC7630.

The yhjH gene was obtained by PCR using *E. coli* MG1655 chromosomal DNA and primers P7 (SEQ ID NO: 15) and P8 (SEQ ID NO: 16). Primer P7 contains 21 nucleotides homologous to the 5'-region of cat gene required for further joining with yhjH gene. Primer P8 contains 40 nucleotides homologous to the region located downstream to TAA codon of intB gene required for further integration into the bacterial chromosome.

The DNA fragment containing chloramphenicol resistance marker ($Cm^R$) encoded by cat gene was obtained by PCR using the commercially available plasmid pACYC 184 (GenBank/EMBL accession number X06403, "Fermentas", Lithuania) as the template and primers P9 (SEQ ID NO: 17) and P10 (SEQ ID NO: 18). Primer P9 contains 41 nucleotides homologous to the region located upstream to ATG codon of intB gene required for further integration into the bacterial chromosome. Primer P10 contains 21 nucleotides homologous to the 5'-region of $P_{yhjH}$ promoter required for further joining with yhjH gene.

PCR was provided using the "GeneAmp PCR System 2700" thermal cycler (Applied Biosystems). The reaction mixture with total volume of 50 µl consisted of 5 µl of 10×PCR-buffer with 25 mM $MgCl_2$ ("Fermentas", Lithuania), 200 µM each of dNTP, 25 pmol each of the exploited primers and 1 U of Taq-polymerase ("Fermentas", Lithuania). Approximately 5 ng of the plasmid DNA was added into the reaction mixture as a template DNA for the PCR amplification. The temperature profile was the following: initial DNA denaturation for 5 min at 95° C. followed by 25 cycles of: denaturation at 95° C. for 30 sec, annealing at 54° C. for 30 sec and elongation at 72° C. for 45 sec for yhjH gene or 50 sec for the cat gene; and the final elongation for 5 min at 72° C. Then, the amplified DNA fragment was purified by agarose gel-electrophoresis, extracted using "GenElute Spin Columns" ("Sigma", USA) and precipitated by ethanol.

The cat-$P_{yhjH}$-yhjH DNA fragment was obtained by overlapping PCR using the two above-described DNA fragments and primers P8 (SEQ ID NO: 16) and P9 (SEQ ID NO: 17). The amplified cat-$P_{yhjH}$-yhjH DNA fragment was purified by agarose gel-electrophoresis as described. The obtained DNA fragment was used for electroporation and Red-mediated integration into the bacterial chromosome of the *E. coli* MG1655::Δtdh,rhtA*/pKD46 (see Example 1).

The MG1655::Δtdh,rhtA*/pKD46 cells were grown, diluted; and further grown as well as electroporation were performed as described in Example 1.

Shocked cells were added to 1 ml of the SOC-medium (Sambrook et al, "Molecular Cloning A Laboratory Manual, $2^{nd}$ ed.", Cold Spring Harbor Laboratory Press (1989)), incubated 2 hours at 37° C. and then spread onto L-agar containing 20 µg/ml of chloramphenicol.

Colonies grown within 24 h were tested for the presence of the cat-$P_{yhjH}$-yhjH DNA fragment instead of the native intB gene by PCR using primers P11 (SEQ ID NO: 19) and P12 (SEQ ID NO: 20). For this purpose, a freshly isolated colony was suspended in 20 µl water, and then 1 µl of obtained suspension was used for PCR. The temperature profile was the following: initial DNA denaturation for 10 min at 95° C. followed by 30 cycles of: denaturation at 95° C. for 30 sec, annealing at 55° C. for 30 sec and elongation at 72° C. for 2 min; and the final elongation for 5 min at 72° C. A few $Cm^R$ colonies tested contained the desired 2215 bp DNA fragment, confirming presence of the cat-$P_{yhjH}$-yhjH DNA fragment instead of the 1620 bp native intB gene (FIG. 2). One of the obtained strains was cured from the thermosensitive plasmid pKD46 by culturing at 37° C., and the resulting strain was named as *E. coli* MG1655::Δtdh,rhtA*,ΔintB::yhjH,cat.

Example 4

Construction of the *E. coli* MG1655::Δtdh,rhtA*, $P_{tac7}$flhDC,ΔintB::yhjH,cat Strain The *E. coli* MG1655::Δtdh,rhtA*,$P_{tac7}$flhDC,ΔintB:: yhjH,cat strain was obtained by the method of general transduction of the ΔintB::yhjH mutation from the MG1655:: Δtdh,rhtA*,ΔintB::yhjH,cat strain into the MG1655::Δtdh, rhtA*,$P_{tac7}$flhDC strain (Miller J. H. (1972) Experiments in Molecular Genetics, Cold Spring Harbor Lab. Press, Plainview, N.Y.). For this purpose, the MG1655::Δtdh,rhtA*, $P_{tac7}$flhDC strain was infected with a bacterial phage $P1_{vir}$ grown on the donor MG1655::Δtdh,rhtA*,ΔintB::yhjH,cat strain. Thus, the MG1655::Δtdh,rhtA*,$P_{tac7}$flhDC,ΔintB:: yhjH,cat strain was obtained.

Example 5

Production of L-threonine by the *E. coli* MG1655:: Δtdh,rhtA*,$P_{tac7}$flhDC,ΔintB::yhjH,cat Strain The parent strain MG1655::Δtdh,rhtA*,$P_{tac7}$flhDC and MG1655::Δtdh,rhtA*,$P_{tac7}$flhDC,ΔintB::yhjH,cat were each transformed by plasmid pVIC40 (see Example 2). Strains obtained were cultivated at 37° C. for 18 hours in a nutrient broth, then 0.1 ml of each of the obtained cultures was inoculated into 2 ml of fermentation medium in a 20×200 mm test-tube and cultivated at 37° C. for 24 hours on a rotary shaker. The fermentation medium composition and preparation, the method of L-threonine estimation are described in Example 2.

The results of 20 independent test-tube fermentations (as average values) are shown in Table 2. As it can be seen from the Table 2, the modified *E. coli* MG1655::Δtdh,rhtA*, $P_{tac7}$flhDC,ΔintB::yhjH,cat strain caused the higher amount of accumulation of L-threonine as compared with the parent *E. coli* MG1655::Δtdh,rhtA*,$P_{tac7}$flhDC strain.

TABLE 2

| Strain | 24 h | | |
|---|---|---|---|
| | $OD_{600}$ | Thr, g/l | Thr/$OD_{600}$, g/l |
| MG1655::Δtdh, rhtA*, $P_{tac7}$flhDC(pVIC40) | 12.0 ± 0.3 | 7.0 ± 0.5 | 0.58 |
| MG1655::Δtdh, rhtA*, $P_{tac7}$flhDC, ΔintB::yhjH, cat(pVIC40) | 11.9 ± 0.2 | 8.1 ± 0.5 | 0.68 |

Example 6

Construction of the *E. coli* MG1655::Δtdh,rhtA*, $P_{tac7}$fliZ,cat Strain

Figure 3:
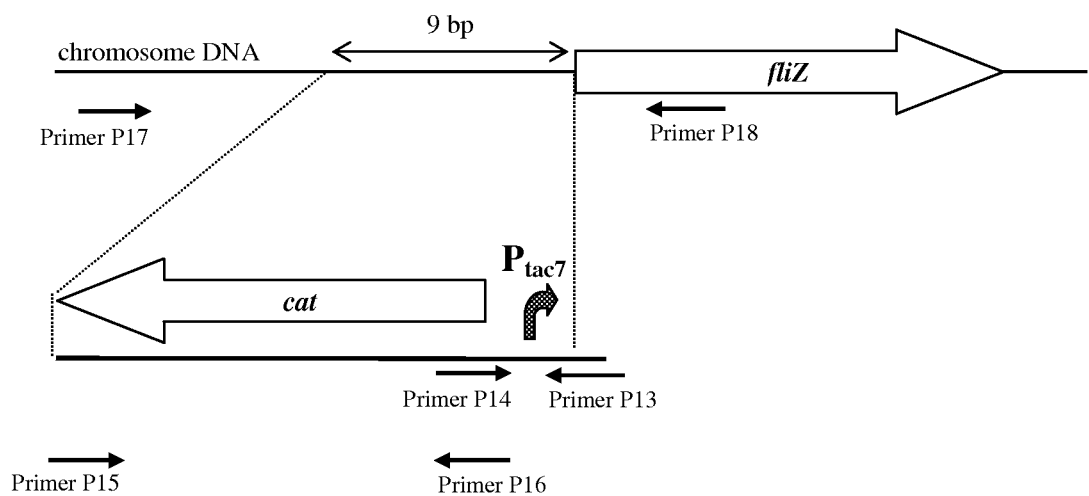
FIG. 3 is a scheme for the cat-P$_{tac7}$ DNA fragment construction.

The *E. coli* MG1655::Δtdh,rhtA*,$P_{tac7}$fliZ,cat strain was constructed in the same manner as described for the MG1655::Δtdh,rhtA*,$P_{tac7}$flhDC strain in Example 1 (FIG. 3).

The $P_{tac7}$ promoter fragment was obtained by PCR using the commercially available plasmid pKK223-3 ("Pharmacia") as a template and primers P13 (SEQ ID NO: 21) and P14 (SEQ ID NO: 22). Primer P13 contains 40 nucleotides homologous to the 5'-region of fliZ gene required for further integration into the bacterial chromosome. In addition, primer P13 has a deletion of C-nucleotide (the $23^{rd}$ position upstream to ATG codon) in LacI-binding site region. Primer P14 contains 21 nucleotides homologous to the 5'-region of cat gene required for further joining with $P_{tac7}$ promoter.

The DNA fragment containing chloramphenicol resistance marker ($Cm^R$) encoded by cat gene was obtained by PCR using the commercially available plasmid pACYC 184 (GenBank/EMBL accession number X06403, "Fermentas", Lithuania) as the template and primers P15 (SEQ ID NO: 23) and P16 (SEQ ID NO: 24). Primer P15 contains 41 nucleotides homologous to the region located 9 bp upstream to the start codon of fliZ gene required for further integration into the bacterial chromosome. Primer P16 contains 21 nucleotides homologous to the 5'-region of $P_{tac7}$ promoter required for further joining with cat gene.

The cat-fliZ DNA fragment was obtained by overlapping PCR using the two above-described DNA fragments and primers P15 (SEQ ID NO: 23) and P13 (SEQ ID NO: 21) and used for electroporation and integration into the bacterial chromosome of the E. coli MG1655::Δtdh,rhtA*/pKD46.

Colonies grown within 24 h were tested for the presence of $Cm^R$ marker instead of the native promoter region of fliZ gene by PCR using primers P17 (SEQ ID NO: 25) and P18 (SEQ ID NO: 26) as described in Example 3. A few $Cm^R$ colonies tested contained the desired 1540 bp DNA fragment, confirming presence of the $Cm^R$ marker DNA instead of the 295 bp native promoter region of fliZ gene (FIG. 3). One of the obtained strains was cured from the thermosensitive plasmid pKD46 by culturing at 37° C., and the resulting strain was named as E. coli MG1655::Δtdh,rhtA*,$P_{tac7}$fliZ,cat.

Example 7

Construction of the E. coli MG1655::Δtdh,rhtA*, $P_{tac7}$flhDC,$P_{tac7}$fliZ,cat Strain The E. coli MG1655::Δtdh,rhtA*,$P_{tac7}$flhDC,$P_{tac7}$fliZ,cat strain was obtained by the method of general transduction of the $P_{tac7}$fliZ mutation from the MG1655::Δtdh,rhtA*,$P_{tac7}$fliZ,cat strain into the MG1655::Δtdh,rhtA*,$P_{tac7}$flhDC strain (Miller J. H. (1972) Experiments in Molecular Genetics, Cold Spring Harbor Lab. Press, Plainview, N.Y.). For this purpose, the MG1655::Δtdh,rhtA*,$P_{tac7}$flhDC strain was infected with a bacterial phage $P1_{vir}$ grown on the donor MG1655::Δtdh,rhtA*,$P_{tac7}$fliZ,cat strain. Thus, the MG1655::Δtdh,rhtA*,$P_{tac7}$flhDC,$P_{tac7}$fliZ,cat strain was obtained.

Example 8

Production of L-threonine by the E. coli MG1655:: Δtdh,rhtA*,$P_{tac7}$flhDC, $P_{tac7}$fliZ,cat Strain The parent strain MG1655::Δtdh,rhtA*,$P_{tac7}$flhDC and MG1655::Δtdh,rhtA*,$P_{tac7}$flhDC,$P_{tac7}$fliZ,cat were each transformed by plasmid pVIC40 (see Example 2). Strains obtained were cultivated at 37° C. for 18 hours in a nutrient broth. Then 0.1 ml of each of the obtained cultures was inoculated into 2 ml of fermentation medium in a 20×200 mm test-tube and cultivated at 37° C. for 24 hours on a rotary shaker. The fermentation medium composition and preparation, and the method of L-threonine estimation are described in Example 2.

The results of 20 independent test-tube fermentations (as average values) are shown in Table 3. As it can be seen from the Table 3, the modified E. coli MG1655::Δtdh,rhtA*, $P_{tac7}$flhDC,$P_{tac7}$fliZ,cat strain caused the higher amount of accumulation of L-threonine as compared with the parent E. coli MG1655::Δtdh,rhtA*,$P_{tac7}$flhDC strain.

TABLE 3

| | 24 h | | |
|---|---|---|---|
| Strain | $OD_{600}$ | Thr, g/l | Thr/$OD_{600}$, g/l |
| MG1655::Δtdh, rhtA*, $P_{tac7}$flhDC (pVIC40) | 12.0 ± 0.3 | 7.0 ± 0.5 | 0.58 |

TABLE 3-continued

| | 24 h | | |
|---|---|---|---|
| Strain | $OD_{600}$ | Thr, g/l | Thr/$OD_{600}$, g/l |
| MG1655::Δtdh, rhtA*, $P_{tac7}$flhDC, $P_{tac7}$fliZ, cat(pVIC40) | 11.5 ± 0.3 | 9.3 ± 0.6 | 0.81 |

Example 9

Construction of the E. coli AJ12739::$P_{tac7}$flhDC, $Km^R$ Strain

The E. coli AJ12739::$P_{tac7}$flhDC,$Km^R$ strain was obtained by the transduction of the $P_{tac7}$flhDC mutation from the MG1655::Δtdh,rhtA*,$P_{tac7}$flhDC strain into the L-phenylalanine-producing strain AJ12739 (tyrA::Tn10, tyrR) (VKPM B-8197) (U.S. Pat. No. 7,666,655). For this purpose, the AJ12739 strain was infected with a bacterial phage $P1_{vir}$ grown on the donor MG1655::Δtdh,rhtA*,$P_{tac7}$flhDC,$Km^R$ strain. Thus, the AJ12739::$P_{tac7}$flhDC,$Km^R$ strain was obtained. The AJ12739 strain was deposited on Nov. 6, 2001 in the Russian National Collection of Industrial Microorganisms (VKPM) (Russian Federation, 117545 Moscow, 1 Dorozhny proezd 1) under the accession number B-8197.

Example 10

Production of L-Phenylalanine by the E. coli AJ12739::$P_{tac7}$flhDC,$Km^R$ Strain The parent strain AJ12739 and the phenylalanine-producing strain AJ12739::$P_{tac7}$flhDC,$Km^R$ were each cultivated at 37° C. for 18 hours in a nutrient broth with 100 mg/l ampicillin. Then 0.3 ml of the obtained culture was inoculated into 3 ml of a fermentation medium containing 100 mg/l ampicillin in a 20×200 mm test tube and cultivated at 37° C. for 48 hours on a rotary shaker.

The fermentation medium contained (g/l):

| | |
|---|---|
| Glucose | 40 |
| $(NH_4)_2SO_4$ | 16 |
| $K_2HPO_4$ | 0.1 |
| $MgSO_4 \cdot 7H_2O$ | 1.0 |
| $MnSO_4 \cdot 5H_2O$ | 0.01 |
| $FeSO_4 \cdot 7H_2O$ | 0.01 |
| Thiamine hydrochloride | 0.0002 |
| Yeast extract | 2.0 |
| L-Tyrosine | 0.125 |
| $CaCO_3$ | 30 |

Glucose and magnesium sulfate were sterilized separately. $CaCO_3$ was dry-heat sterilized at 180° C. for 2 hours. The pH was adjusted to 7.0. Antibiotic was introduced into the medium after sterilization.

After cultivation, accumulated L-phenylalanine was measured using thin-layer chromatography (TLC). TLC plates (10×15 cm) were coated with 0.11 mm layers of Sorbfil silica gel containing non-fluorescent indicator (Sorbpolymer, Krasnodar, Russian Federation). Samples were applied to the plates with the Camag Linomat 5 sample applicator. The Sorbfil plates were developed with a mobile phase consisting of propan-2-ol/ethylacetate/25% aqueous ammonia/water=40/40/7/16 (v/v). A solution of ninhydrin (2%, w/v) in acetone was used as the visualizing reagent. After development, plates were dried and scanned with the Camag TLC Scanner 3 in absorbance mode with detection at 520 nm using winCATS software (version 1.4.2).

The results of 20 independent test-tube fermentations (as average values) are shown in Table 4. As it can be seen from the Table 4, the modified *E. coli* AJ12739::P$_{tac7}$flhDC,Km$^R$ strain caused the higher amount of accumulation of L-phenylalanine as compared with the parent *E. coli* AJ12739 strain.

TABLE 4

| Strain | 48 h | | |
|---|---|---|---|
| | OD$_{600}$ | Phe, g/l | Phe/OD$_{600}$, g/l |
| AJ12739 | 8.3 ± 0.2 | 1.6 ± 0.1 | 0.19 |
| AJ12739::P$_{tacC7}$flhDC, Km$^R$ | 7.1 ± 0.3 | 2.2 ± 0.3 | 0.31 |

While the invention has been described in detail with reference to preferred embodiments thereof, it will be apparent to one skilled in the art that various changes can be made, and equivalents employed, without departing from the scope of the invention. All the cited references herein are incorporated as a part of this application by reference.

INDUSTRIAL APPLICABILITY

According to the present invention, an L-amino acid is efficiently produced by a bacterium belonging to the family Enterobacteriaceae.

The invention claimed is:

1. A method for producing an L-amino acid comprising culturing an *Escherichia coli* bacterium in a medium, and collecting the L-amino acid from the medium,
wherein the bacterium is able to produce an L-amino acid and has been modified so that expression of either the flhD gene or flhC gene, or both, is/are enhanced by a method selected from the group consisting of: a) increasing the copy number of the gene(s), b) modifying an expression control region of the gene(s), and c) combinations thereof;

wherein the flhD gene encodes a protein selected from the group consisting of:

(A) a protein comprising the amino acid sequence shown in SEQ ID NO: 2;

(B) a protein comprising the amino acid sequence shown in SEQ ID NO: 2, but wherein one to five amino acid residues are substituted, deleted, inserted, added or inverted, and said protein has DNA-binding transcriptional dual regulator activity according to the amino acid sequence of SEQ ID NO: 2, and (C) a protein comprising an amino acid sequence having an identity of 90% or higher to the amino acid sequence of SEQ ID NO: 2, and said protein has DNA-binding transcriptional dual regulator activity according to the amino acid sequence of SEQ ID NO: 2, and (D) combinations thereof;

wherein the flhC gene encodes a protein selected from the group consisting of:

(i) a protein comprising the amino acid sequence shown in SEQ ID NO: 4, (ii) a protein comprising the amino acid sequence shown in SEQ ID NO: 4, but wherein one to five amino acid residues are substituted, deleted, inserted, added or inverted, and said protein has DNA-binding transcriptional dual regulator activity according to the amino acid sequence of SEQ ID NO: 4, (iii) a protein comprising an amino acid sequence having an identity of 90% or higher to the amino acid sequence of SEQ ID NO: 4, and said protein has DNA-binding transcriptional dual regulator activity according to the amino acid sequence of SEQ ID NO: 4, and (iv) combinations thereof.

2. The method according to claim 1, wherein the bacterium has been further modified to enhance expression of at least one gene selected from the group consisting of a) the yhjH gene, b)the fliZ gene, and c) combinations thereof.

3. The method according to claim 2, wherein the yhjH gene encodes a protein selected from the group consisting of:

(A) a protein comprising the amino acid sequence shown in SEQ ID NO: 6, (B) a protein comprising the amino acid sequence shown in SEQ ID NO: 6, but wherein one to five amino acid residues are substituted, deleted, inserted, added or inverted, and said protein has cyclic-di-GMP phosphodiesterase activity according to the amino acid sequence of SEQ ID NO: 6, (C) a protein comprising an amino acid sequence having an identity of 90% or higher to the amino acid sequence of SEQ ID NO: 6, and said protein has cyclic-di-GMP phosphodiesterase activity according to the amino acid sequence of SEQ ID NO: 6, and (D) combinations thereof.

4. The method according to claim 2, wherein the fliZ gene encodes a protein selected from the group consisting of:

(A) a protein comprising the amino acid sequence shown in SEQ ID NO: 8, (B) a protein comprising the amino acid sequence shown in SEQ ID NO: 8, but wherein one to five amino acid residues are substituted, deleted, inserted, added or inverted, and said protein has regulator activity according to the amino acid sequence of SEQ ID NO: 8, (C) a protein comprising an amino acid sequence having an identity of 90% or higher to the amino acid sequence of SEQ ID NO: 8, and said protein has regulator activity according to the amino acid sequence of SEQ ID NO: 8, and (C) combinations thereof.

5. The method according to claim 1, wherein said L-amino acid is an aromatic L-amino acid.

6. The method according to claim 5, wherein said aromatic L-amino acid is selected from the group consisting of L-phenylalanine, L-tyrosine, L-tryptophan, and combinations thereof.

7. The method according to claim 1, wherein said L-amino acid is a non-aromatic L-amino acid.

8. The method according to claim 7, wherein said non-aromatic L-amino acid is selected from the group consisting of L-threonine, L-lysine, L-cysteine, L-methionine, L-leucine, L-isoleucine, L-valine, L-histidine, L-serine, L-alanine, L-asparagine, L-aspartic acid, L-glutamine, L-glutamic acid, L-proline, L-arginine, glycine, and combinations thereof.

9. The method according to claim 1, wherein said L-amino acid is L-phenylalanine.

10. The method according to claim 1, wherein said L-amino acid is L-threonine.

* * * * *